US007009042B1

(12) United States Patent
Skeiky et al.

(10) Patent No.: US 7,009,042 B1
(45) Date of Patent: Mar. 7, 2006

(54) **METHODS OF USING A *MYCOBACTERIUM TUBERCULOSIS* CODING SEQUENCE TO FACILITATE STABLE AND HIGH YIELD EXPRESSION OF THE HETEROLOGOUS PROTEINS**

(75) Inventors: Yasir Skeiky, Seattle, WA (US); Jeffrey Guderian, Lynnwood, WA (US)

(73) Assignee: Corixa Corporation, Seattle, WA (US)

( * ) Notice: Subject to any disclaimer, the term of this patent is extended or adjusted under 35 U.S.C. 154(b) by 668 days.

(21) Appl. No.: 09/684,215

(22) Filed: Oct. 6, 2000

Related U.S. Application Data

(60) Provisional application No. 60/158,585, filed on Oct. 7, 1999.

(51) Int. Cl.
*C07H 21/04* (2006.01)
*A61K 38/00* (2006.01)

(52) U.S. Cl. ............... 536/23.1; 435/69.1; 435/455; 435/320.1; 514/2

(58) Field of Classification Search ............ 536/23.1, 536/23.4, 23.5, 23.7; 435/69.1, 320.1, 455, 435/69.7; 530/350, 412, 387.9; 424/192.1; 514/2, 44
See application file for complete search history.

(56) References Cited

U.S. PATENT DOCUMENTS

| | | | | |
|---|---|---|---|---|
| 6,133,023 | A * | 10/2000 | Madsen et al. ............ | 435/320.1 |
| 6,270,772 | B1 * | 8/2001 | Burrows et al. ........... | 424/195.1 |
| 6,350,456 | B1 * | 2/2002 | Reed et al. ............... | 424/248.1 |
| 6,509,448 | B1 * | 1/2003 | Wang et al. .............. | 530/387.9 |
| 6,544,522 | B1 * | 4/2003 | Skeiky et al. ............. | 424/190.1 |
| 6,566,072 | B1 * | 5/2003 | Watson et al. ............. | 435/7.1 |
| 6,627,198 | B1 * | 9/2003 | Reed et al. ............... | 424/190.1 |

FOREIGN PATENT DOCUMENTS

| | | |
|---|---|---|
| WO | WO 97/09429 | 3/1997 |
| WO | WO 9709428 * | 3/1997 |
| WO | WO 98/16645 | 4/1998 |
| WO | WO 99/09186 | 2/1999 |
| WO | WO 99/42076 | 8/1999 |
| WO | WO 99/42118 | 8/1999 |
| WO | WO 99/51748 | 10/1999 |

OTHER PUBLICATIONS

Adams, R. L. P. et al. (1986) in "Biochemistry of the nucleic acid" p. 469, Chapman and Hall, London.*
Ngo, J. T. et al. et al. (1994) "Computational complexity protein structure prediction, and the levinthal paradox". in "The protein folding problem and tertiary structure prediction". p. 491-495, Merz, Jr. K. et al. Eds. Birkhauser, Boston.*
Yan, Z. et al. (1999) Mass spectrometric determination of a novel modification of the N-terminus of histidine-tagged proteins expressed in bacteria. Biochem. Biophys. Res. Commun. vol. 259, pp. 271-282.*

* cited by examiner

*Primary Examiner*—Jon Weber
*Assistant Examiner*—Samuel W. Liu
(74) *Attorney, Agent, or Firm*—Townsend and Townsend and Crew LLP

(57) ABSTRACT

The present invention relates generally to nucleic acid and amino acid sequences of a fusion polypeptide comprising a *Mycobacterium tuberculosis* polypeptide, and a heterologous polypeptide of interest, expression vectors and host cells comprising such nucleic acids, and methods for producing such fusion polypeptides. In particular, the invention relates to materials and methods of using such *M. tuberculosis* sequence as a fusion partner to facilitate the stable and high yield expression of recombinant heterologous polypeptides of both eukaryotic and prokaryotic origin.

24 Claims, 12 Drawing Sheets

```
GACTACGTTGGTGTAGAAAAATCCTGCCGCCCGGACCCCTTAAGGCTGGGACAATTTCTGATAGCTACCCCGACACAGAGGTTACGGGATGAGCA         95
                                                                              |--SD--|       |-------
                                                                                              M  S

ATTCGCGCCGCCGCTCACTCAGGTGGTCATGGTTGCTGAGCGTGTCGCTGCCGTCGGGCCTGGCCTGGCTGCCGTCGGCCACGGCGCCCCG        190
----SIGNAL SEQUENCE---------------------------------------------------------------|MTB32A
 N  S  R  R  R  S  L  R  W  S  W  L  L  S  V  L  A  A  V  G  L  G  L  A  T  A  P  A  P

CCGGCCTTGTCGCAGGACCGGTTCGCCGACTTCCCCGCACTGCCCCTCGACCCGTCCGCGATGGTCGCCCAAGTGGGCCCACAGGTGGTCAACAT        285
-------MTB322A
 P  A  L  S  Q  D  R  F  A  D  F  P  A  L  P  L  D  P  S  A  M  V  A  Q  V  G  P  Q  V  V  N  I

CAACACCAAACTGGGCTACAACAACGCCGTGGGCGCCGGAACCGGCATCGTCATCGATCCCAACGGTGTCGTGCTGACCAACAACCACGTGATCG        380
-----MTB322A
 N  T  K  L  G  Y  N  N  A  V  G  A  G  T  G  I  V  I  D  P  N  G  V  V  L  T  N  N  H  V  I

CGGGGCGCCACCGACATCAATGCGTTCAGCGTCGGCTCCGGCCAAACCTACGGCGTCGATGTGGTCGGGTATGACCGCACCCAGGATGTCGCGGTG        475
                                                                        ----MTB322A
 A  G  A  T  D  I  N  A  F  S  V  G  S  G  Q  T  Y  G  V  D  V  V  G  Y  D  R  T  Q  D  V  A  V

CTGCAGCTGCGCGGGGCATTCTTCCTGCCGTCGGCCGCGATCGGTTCGGCGGCGTTGGTGAGCGTCGGTGATGGGCAACAGCGGTGG        570
---------MTB322A
 L  Q  L  R  G  A  F  F  L  P  S  A  A  I  G  G  G  V  A  V  G  E  P  V  V  A  M  G  N  S  G  G

GCAGGGCGGGAACGCCCCCGTGCGCTGCCTGGCGTCGCAGGGTGGTCGCCGAAAACCGTGCAGGCGCGTCGACCGGTGACGCCGAAGAGACAT        665
----MTB322A
 Q  G  G  T  P  R  A  V  P  G  R  V  V  A  L  G  Q  T  V  Q  A  S  D  S  L  T  G  A  E  E  T

TGAACGGGTTGATCCAGTTCGATGCCGCGGCGATCCAGCCGGTGATTCGGGGCGGGCCCGTCGTCAACGGCCTAGGACAGGTGGTCGGTATGAACACG        760
----MTB322A
 L  N  G  L  I  Q  F  D  A  A  A  I  Q  P  G  D  S  G  G  P  V  V  N  G  L  G  Q  V  V  G  M  N
```

FIG. 1A.

```
GCCGGCGTCCGATAACTTCCAGCTGTCCCAGGGTGGGCAGGGATTCGCCATTCCGATCGGGCAGGGCGATGCGGCAGATCCGATCGGG    855
      ----|----|----|----|----|----|----|----|----|----|----|----|----|----|----|----|
      A  A  S  D  N  F  Q  L  S  Q  G  G  Q  G  F  A  I  P  I  G  Q  A  M  A  I  A  G  Q  I  R  S  G
                                                            ---MTB322A---

TGGGGGTCACCCACCGTTCATATCGGGCCTTCCTCGGCTTGGGTGTTGTCGACAACAACGGCAACGGCACGAGTCCAACGCGTGG    950
      ----|----|----|----|----|----|----|----|----|----|----|----|----|----|----|----|
      G  G  S  P  T  V  H  I  G  P  T  A  F  L  G  L  G  V  V  D  N  N  G  N  F  A  R  V  Q  R  V
                                                            ---MTB322A---

TCGGGAGCGCTCCGGCGCAAGTCTCGGCATCTCCACCGGCGACGTGATCACCGCGGTCGACGGCGCTCCGATCAACTGGCCGATGGCG    1045
      ----|----|----|----|----|----|----|----|----|----|----|----|----|----|----|----|
      V  G  S  A  P  A  A  S  L  G  I  S  T  G  D  V  I  T  A  V  D  G  A  P  I  N  S  A  T  A  M  A
                                                            ---MTB322A---

GACGCGCTTAACGGGCATCATCCCGGTCGACGTCATCTCGGTGACCTGGCAAACCAAGTCGGGCGGCACGCGTACAGGGAACGTGACATTGGCCGA    1140
      ----|----|----|----|----|----|----|----|----|----|----|----|----|----|----|----|
      D  A  L  N  G  H  H  P  G  D  V  I  S  V  T  W  Q  T  K  S  G  G  T  R  T  G  N  V  T  L  A
                                                            ---MTB322A---

GGGACCCCCGGCCTGATTCGTCGCGGATACCACCCCGCCGGCCAATTGGATTGGCGCCAGCCGTGATTGCCGCGTGAGCCCCGAGTTCCG    1235
      ----|----|----|----|----|----|----|----|----|----|----|----|----|----|----|----|
      ---MTB322A--->
      E  G  P  P  A

TCTCCCGTGCGCTGGCATCGTGGAAGCAATGAACGAGGCAGAACACAGCGTCGAGCCACCCTCCCGTGCAGGGCAGTCACGTCGAAGGCGGTGTG    1330
GTCGAGCATCCGGATGCCAAGGACTTCGGCCAGCCGTTCGGCCACGCCGTCTCTTAAGCACGCGTCCGATCCGTGGTTTAAGCACGAGAGTGCTGT    1425
CCGGGCCGTTCTTCGACGCCAGCGGTTCCGGCGACGTCGACTCGCCCTCGACTACCTGCCTGGCTTGGCATCGACTGCA    1520
TCTGGTTGCCGCGTTCGCCGATTCTACGACGGCGGTTACGACCATTCGCGACTTCTACAAGGTGCTGCCCGAATTCGGCACCGTCGAC    1615
GATTCGTCGCCTGTCGCCCGAGTCGACGCGCTCACCGGCGAGTATCGCCATCATCACGACCTGGTGATGAATCACACCTCGGAGTCGCACCCCTGTT    1710
TCAGGAGTCCCGCCGCTACGACCCGTACGGTGACTATTACGTGTGGAGCGACACCAGCGAGCGCTACACCGAGCCCGACGCCCGGATCATCTTCG    1805
TCGACACCGAAGAGTCGAACTGGTCATTCGCCCGACAGTTCTACTGGCACCGATTCTT    1872
```

*FIG. 1B.*

```
ACGGCCGCGTCCGATAACTTCCAGCTGTCCCAGGGTGGCCAGGGATTCGCCATTCCGATCGGGCAGGCGATGGCGA
|-----------------------------------------Ra12-------------------------------|
 T  A  A  S  D  N  F  Q  L  S  Q  G  G  Q  G  F  A  I  P  I  G  G  A  M  A

TCGCGGGCCAGATCCGATCGGGTGGGGGTCACCCCAACCGTTCATATCGGCCTACCGCCTTCCTCGGCTTGGGTGTTGTCGACAACAACGGCAACGGCGC
|-----------------------------------------Ra12-------------------------------------------------------|
 I  A  G  Q  I  R  S  G  G  G  S  P  T  V  H  I  G  P  T  A  F  L  G  L  G  V  V  D  N  N  G  N  G  A

ACGAGTCCAACGCGTGGTCGGGAGCGCTCCGGGCGGCAAGTCTCGGCCATCTCCACCGGCGACGTGATCACCGCGGTCGACGGCGCTCCGATCAACTCGGCC
|-----------------------------------------Ra12------------------------------------------------------|
 R  V  Q  R  V  V  G  S  A  P  A  A  S  L  G  I  S  T  G  D  V  I  T  A  V  D  G  A  P  I  N  S  A

ACCGCGGATGGCGGACGCGCTTAACGGGCATCATCCCGGTGACGTCATCTCGGTGACCTGGCAAACCAAGTCGGGCGGCACGCGTACAGGAACGTGACAT
|------------------------------------------Ra12-----------------------------------------------------|
 T  A  M  A  D  A  L  N  G  H  H  P  G  D  V  I  S  V  T  W  Q  T  K  S  G  G  T  R  T  G  N  V  T

TGGCCCGAGGGACCCCCCGGCC
|-------Ra12--------|
 L  A  E  G  P  P  A
```

FIG. 2.

```
CATATGCATCACCATCACCATCACACGGGCCGCGTCCGATAACTTCCAGGTGTGGGCAGGGATTCGCCATTCCGATCGGGCAGGCGAT    95
|----Met (6xHis)----|||----------------------------------------Ra12--------------------|
     M   H   H   H   H   H   H   T   A   A   S   D   N   F   Q   L   S   Q   G   G   Q   G   F   A   I   P   I   G   Q   A   M

GGCGATCGCGGGCCAGATCGGGTGGGGGTCACCGGCCTTCATATCGGGCTTGTGTCGACAACG    190
|----------------------------------------Ra12--------------------|
  A   I   A   G   Q   I   R   S   G   G   G   S   P   T   V   H   I   G   P   T   A   F   L   G   L   G   V   V   D   N   N

GCAACGGGCGACGAGTCCAAGCGTGGTCGGAGCGCTCCGGCGGCAAGTCTCCGGCATCTCCACCGGCGACGTGATCACCGGCGGTCGACGGCGCT    285
|----------------------------------------Ra12--------------------|
  G   N   G   A   R   V   Q   R   V   V   G   S   A   P   A   A   S   L   G   I   S   T   G   O   V   I   T   A   V   D   G   A

CCGATCAACTCGGCCACCGCGATGGCGGACGCGCTTAACGGGCATCATCCGGTGACGTCATCTCGGTGACCTGGCAAACCAAGTCGGGGCCAC    380
|----------------------------------------Ra12--------------------|
  P   I   N   S   A   T   A   M   A   D   A   L   N   G   H   H   P   G   O   V   I   S   V   T   W   Q   T   K   S   G   G   T

GCGTACAGGGAACGTGACATTGGCCGAGGGACCCCCCGAATTGACGACGACAAGGATCCACCTGACCCCGCATCAGCCGGACATGACGA    475
|----------------------------------------Ra12--------------------|  |EcoR|Enterokinase|          |----DPPD----|
  R   T   G   N   V   T   L   A   E   G   P   P   A   E   F   D   D   D   D   K   D   P   P   D   P   H   Q   P   D   M   T AAGGCTATTGCCCGGGTGGCCGATGGGGTTTTGGCCGACTTGGCCGTGTGCGACGGCGAGAAGTACCCCGACGGCTCGTTTTGGCACCAGTGGATG    570
                                                                                                  |----DPPD----|
  K   G   Y   C   P   G   G   R   W   G   F   G   D   L   A   V   C   D   G   E   K   Y   P   D   G   S   F   W   H   Q   W   M CAAAACGTGGTTTACGGGCCCCACAGTTTACTTCGATTGTGTCAGCGGGTGAGCCCCTCCCCGGCCCCGCCACCGGGTGTTGCGGTGGGGC    665
                                                                                              |----DPPD----|
  Q   T   W   F   T   G   P   Q   F   Y   F   D   C   V   S   G   G   E   P   L   P   G   P   P   P   P   G   G   C   G   G   A AATTCCGTCCGAGCAGCCCAACGCTCCCTGAGAATTC    702
|----DPPD-------→
  I   P   S   E   Q   P   N   A   P
```

```
CAAAACAGGAGGAACCGAGCTGGGGTGCAGAGAACAGTGCCTGAGCGCATTCACCGTTCACTTCTCCGGCCAGTTCACTGGCACAG  760
     ------------------------------------------WT1----------------------------------
  K   Q   E   P   S   W   G   G   A   E   P   H   E   E   Q   C   L   S   A   E   T   V   H   F   S   G   Q   F   T   G   T

CCGGAGCCTGTCGCTACGGGCCCTTCGGTCCTCCTCCGCCCAGCCAGGCCAGGCCAGGCGTCATCCGGGCCAGGATGTTTCCTAACGCGCCCTACCTGCCC  855
     ------------------------------------------WT1----------------------------------
  A   G   A   C   R   Y   G   P   F   G   P   P   P   P   S   Q   A   S   S   G   Q   A   R   M   F   P   N   A   P   Y   L   P

AGCTGCCCTCGAGAGCCAGCCCGCTATTCGCAATCAGGGTTACAGCACGGTTCACCTTCGACGGGACCGCCCAGCTACGGTCACACGCCCTCGCACCA  950
     ------------------------------------------WT1----------------------------------
  S   C   L   E   S   Q   P   A   I   R   N   Q   G   Y   S   T   V   T   F   D   G   T   P   S   Y   G   H   T   P   S   H   H

TGCGGGCAGTTCCCAACCACTCATTCAAGCATGAGGATCCCATGGGCCAGCAGGCTCGCTGGGTGAGCAGCAGTACTCGGTGCCGCCCCCGG  1045
     ------------------------------------------WT1----------------------------------
  A   A   Q   F   P   N   H   S   F   K   H   E   D   P   M   G   -   Q   G   S   L   G   E   Q   Q   Y   S   V   P   P   P

TCTATGGCTGCCACACCCCCACCGACAGCTGCACCGGCAGCCAGGCTTTGCTGCTAAGGACGCCCTACAGCAGTGACAATTTATACCAAATGACA  1140
     ------------------------------------------WT1----------------------------------
  V   Y   G   C   H   T   P   T   D   S   C   T   G   S   Q   A   L   L   L   R   T   P   Y   S   S   D   N   L   Y   Q   M   T

TCCCAGCTTGAATGCATGACCTGGAATCAGATGAACTTAGGAGCCACCTTAAAGGGCCACAGTACGGAGAGCGATAACCACACAACGCC  1235
     ------------------------------------------WT1----------------------------------
  S   Q   L   E   C   M   T   W   N   Q   M   N   L   G   A   T   L   K   G   H   S   T   G   Y   E   S   D   N   H   T   T   P

CATCCCTCTGCGGAGCCCAATACAGAATACACACGCACGGTGTCTTCAGAGGCATTCAGGATGTGCAACGTGTGCCTGGAGTAGCCCGACTCTTG  1330
     ------------------------------------------WT1----------------------------------
  I   L   C   G   A   Q   Y   R   I   H   T   H   G   V   F   R   G   I   Q   D   V   A   R   V   P   G   V   A   P   T   L
```

```
CATATGCATCACCATCACCATCACACGGCCGCGTCCGATAAACTTCCAGCTGTCCCAGGGTGGGCAGGATTCGCCATTCCGATCGGGCAGGCGAT    95
       |----Met(6xHis)----|||----------------------------------Ra12------------------------------|
         M  H  H  H  H  H  H  T  A  A  S  D  N  F  Q  L  S  Q  G  G  Q  G  F  A  I  P  I  G  Q  A  M

GGCGATCGCGGGCCAGATCCGATCGGGTGGGGGTCACCCCAGTCCACATATCGGGCCTTCATATCGGGCCTTCCTCGGCTTGGGTGTGTCGACAACAACG   190
-------------------------------------------Ra12-------------------------------------------------|
   A  I  A  G  Q  I  R  S  G  G  G  S  P  T  V  H  I  G  P  T  A  F  L  G  L  G  V  V  D  N  N

GCAACGGCGCACGAGTCCAACGCGTGGTCGGGAGCGCTCCGGCAGTCTCGGCATCTCCACCGGCGACGTGATCACCGGCGTCGACGGCGCT    285
-------------------------------------------Ra12-------------------------------------------------|
   G  N  G  A  R  V  Q  R  V  V  G  S  A  P  A  A  S  L  G  I  S  T  G  V  I  T  A  V  D  G  A

CCGATCAACTCGGCCACCGCGATGGCGGACGCGCTTAACGGGCATCATCCGGTGACGTCATCTCGGTGACCTGGCAAACCAAGTCGGGGGGCAC    380
-------------------------------------------Ra12-------------------------------------------------|
   P  I  N  S  A  T  A  M  A  D  A  L  N  G  H  H  P  G  Q  V  I  S  V  T  W  Q  T  K  S  G  G  T

GCGTACAGGGAACGTGACATTGGCCGAGGGACCCCGGCGAATTCATCGAGGGAAGGGGCTCTGGCTGCCCCTTATTGGAGAATGTGATTTCCA    475
-----------Ra12---------------------------|| EcoR | Factor Xa |-------------MAMMAGLOBIN---------|
   R  T  G  N  V  T  L  A  E  G  P  P  A  E  F  I  E  G  R  G  S  G  C  P  L  L  E  N  V  I  S AGACAATCAATCCACAAGTGTCTAAGACTGAATACAAAGAACTTCTTCAAGAGTTCATAGACGACAATGCCACTACAAATGCCATAGATGAATTG    570
------------------------------------------MAMMAGLOBIN--------------------------------------------|
   K  T  I  N  P  Q  V  S  K  T  E  Y  K  E  L  L  Q  E  F  I  D  D  N  A  T  T  N  A  I  D  E  L AAGGAAATGTTTCTTAACCAAACGGATGAAACTCTGAGCAATGTTGAGGTGTTTATGCAATTAATATATGACAGCAGTCTTTGTGATTTATTTA    665
------------------------------------------MAMMAGLOBIN-------------------------------------→
   K  E  C  F  L  N  Q  T  D  E  T  L  S  N  V  E  V  F  M  Q  L  I  Y  D  S  S  L  C  D  L  F

AGAATTC    672
```

FIG. 5.

```
ATGCATCACCATCACCATCACACGGCCGCGTCCGATAACTTCCAGCTGTCCCAGGGTGGGCAGGGATTCGCCATTCCGATCGGGCAGGCGATGGC     95
|----Met (6xHis)----||-------------------------Ra12-------------------------------------------
 M  H  H  H  H  H  H  T  A  A  S  D  N  F  Q  L  S  Q  G  G  Q  G  F  A  I  P  I  G  Q  A  M  A

GATCGCGGGCCAGATCCGGTCGGGTGGGGGTGGCACCCGCGTTCATATCGGGCCACCACCGTTCCTCGGCTTGGTGTTGTCGACAACGGCA        190
------------------------------------------Ra12-----------------------------------------------
 I  A  G  Q  I  R  S  G  G  G  G  S  P  T  V  H  I  G  P  T  A  F  L  G  L  G  V  V  D  N  N  G

ACGGGCGCACGAGTCCAACGCGTGGTCGGGAGCGCTCCGGCGCAAGTCTCGGCCATCTCCACCGGCGACGTGATCACCGGTCGACGGCGCTCCG     285
-----------------------------------------Ra12------------------------------------------------
 N  G  A  R  V  Q  R  V  V  G  S  A  P  A  A  S  L  G  I  S  T  G  Q  V  I  T  A  V  D  G  A  P

ATCAACTCGGCCACCGCGATGGCGGACGCGCTTAACGGGCATCATCCCGGTGACGTCATCTCGGTGACCTGCAAACCAAGTCGGGCGCACGCG     380
-----------------------------------------Ra12------------------------------------------------
 I  N  S  A  T  A  M  A  D  A  L  N  G  H  H  P  G  Q  V  I  S  V  T  W  Q  T  K  S  G  G  T  R

TACAGGAACGTGACATTGGCCGAGGGACCCCCGGCCGAATTCATGGTGGATTTCGGGGCGTTACCACCGGAGATCAACTCCGCGAGGATGTACG    475
-----------------------Ra12-----------|EcoRI|-------------------MTB39-------------------------
 T  G  N  V  T  L  A  E  G  P  P  A  E  F  M  V  D  F  G  A  L  P  P  E  I  N  S  A  R  M  Y

CCGGCCCGGGTTCGGCCTCGCTGGTGGCCGCGGACACCGTGGGCGACGTGACCTGTTTTCGGCCCGTCGGCGTTTCAGTCCGTG             570
----------------------------------------MTB39------------------------------------------------
 A  G  P  G  S  A  S  L  V  A  A  A  Q  M  W  D  S  V  A  S  D  L  F  S  A  A  S  A  F  Q  S  V

GTCTGGGGTCTGACGGTCGGGGTCGTGGATAGGTTCGTCGGCCTCGATGGTGGCGGCGGCCTCGCCGTATGTGCGTGATGAGCGTCACCGC      665
--------------------------------------MTB39--------------------------------------------------
 V  W  G  L  T  V  G  S  W  I  G  S  S  A  G  L  M  V  A  A  A  S  P  Y  V  A  W  M  S  V  T  A

GGGGCAGGCCTGAGCTGACCGCCGCCAGTTCCGGGTTGCTGCGGCGGCCTACGAGAGACGGCGTATGGGCTGACGGTGCCCCGCCGGTGATCGCCG  760
----------------------------------------MTB39------------------------------------------------
 G  Q  A  E  L  T  A  A  Q  V  R  V  A  A  A  A  Y  E  T  A  Y  G  L  T  V  P  P  P  V  I  A
```

Ra12(short) polypeptide (SEQ ID NO:17)

TAASDNFQLSQGGQGFAIPIGQAMAIAGQI

FIG. 7.

Ra12(long) polypeptide (SEQ ID NO: 18)

TAASDNFQLSQGGQGFAIPIGQAMAIAGQIKLPTVHIGPTAFLGLGVVDNNGNGARV
QRVVGSAPAASLGISTGDVITAVDGAPINSATAMADALNGHHPGDVISVTWQTKSG
GTRTGNVTLAEGPPA

FIG. 8.

H₃N— | Met | Histag 6aa | Ra12(short) 30aa | HindIII 2aa | human mammaglobin (full length) 93aa | —COO

FIG. 9.

SEQUENCE LISTING

```
<160> NUMBER OF SEQ ID NOS: 23

<210> SEQ ID NO 1
<211> LENGTH: 1872
<212> TYPE: DNA
<213> ORGANISM: Mycobacterium tuberculosis
<220> FEATURE:
<223> OTHER INFORMATION: 32 KD serine protease MTB32A
<220> FEATURE:
<221> NAME/KEY: CDS
<222> LOCATION: (89)..(1156)
<223> OTHER INFORMATION: MTB32A
<220> FEATURE:
<221> NAME/KEY: sig_peptide
<222> LOCATION: (89)..(184)
<223> OTHER INFORMATION: N-terminal hydrophobic secretory signal
      sequence
```

<220> FEATURE:
<221> NAME/KEY: mat_peptide
<222> LOCATION: (185)..(1153)

<400> SEQUENCE: 1

```
gactacgttg gtgtagaaaa atcctgccgc ccggacccct taaggctggga caatttctga         60 tagctacccc gacacaggag gttacggg atg agc aat tcg cgc cgc cgc tca            112
                               Met Ser Asn Ser Arg Arg Arg Ser
                                       -30                -25 ctc agg tgg tca tgg ttg ctg agc gtg ctg gct gcc gtc ggg ctg ggc           160
Leu Arg Trp Ser Trp Leu Leu Ser Val Leu Ala Ala Val Gly Leu Gly
            -20                 -15                 -10 ctg gcc acg gcg ccg gcc cag gcg gcc ccg ccg gcc ttg tcg cag gac           208
Leu Ala Thr Ala Pro Ala Gln Ala Ala Pro Pro Ala Leu Ser Gln Asp
        -5                   -1  1                   5 cgg ttc gcc gac ttc ccc gcg ctg ccc ctc gac ccg tcc gcg atg gtc           256
Arg Phe Ala Asp Phe Pro Ala Leu Pro Leu Asp Pro Ser Ala Met Val
         10                  15                  20 gcc caa gtg ggg cca cag gtg gtc aac atc aac acc aaa ctg ggc tac           304
Ala Gln Val Gly Pro Gln Val Val Asn Ile Asn Thr Lys Leu Gly Tyr
 25                  30                  35                  40 aac aac gcc gtg ggc gcc ggg acc ggc atc gtc atc gat ccc aac ggt           352
Asn Asn Ala Val Gly Ala Gly Thr Gly Ile Val Ile Asp Pro Asn Gly
                 45                  50                  55 gtc gtg ctg acc aac aac cac gtg atc gcg ggc gcc acc gac atc aat           400
Val Val Leu Thr Asn Asn His Val Ile Ala Gly Ala Thr Asp Ile Asn
             60                  65                  70 gcg ttc agc gtc ggc tcc ggc caa acc tac ggc gtc gat gtg gtc ggg           448
Ala Phe Ser Val Gly Ser Gly Gln Thr Tyr Gly Val Asp Val Val Gly
         75                  80                  85 tat gac cgc acc cag gat gtc gcg gtg ctg cag ctg cgc ggt gcc ggt           496
Tyr Asp Arg Thr Gln Asp Val Ala Val Leu Gln Leu Arg Gly Ala Gly
     90                  95                 100 ggc ctg ccg tcg gcg gcg atc ggt ggc ggc gtc gcg gtt ggt gag ccc           544
Gly Leu Pro Ser Ala Ala Ile Gly Gly Gly Val Ala Val Gly Glu Pro
105                 110                 115                 120 gtc gtc gcg atg ggc aac agc ggt ggg cag ggc gga acg ccc cgt gcg           592
Val Val Ala Met Gly Asn Ser Gly Gly Gln Gly Gly Thr Pro Arg Ala
                125                 130                 135 gtg cct ggc agg gtg gtc gcg ctc ggc caa acc gtg cag gcg tcg gat           640
Val Pro Gly Arg Val Val Ala Leu Gly Gln Thr Val Gln Ala Ser Asp
            140                 145                 150 tcg ctg acc ggt gcc gaa gag aca ttg aac ggg ttg atc cag ttc gat           688
Ser Leu Thr Gly Ala Glu Glu Thr Leu Asn Gly Leu Ile Gln Phe Asp
        155                 160                 165 gcc gcg atc cag ccc ggt gat tcg ggc ggg ccc gtc gtc aac ggc cta           736
Ala Ala Ile Gln Pro Gly Asp Ser Gly Gly Pro Val Val Asn Gly Leu
    170                 175                 180 gga cag gtg gtc ggt atg aac acg gcg gcg tcc gat aac ttc cag ctg           784
Gly Gln Val Val Gly Met Asn Thr Ala Ala Ser Asp Asn Phe Gln Leu
185                 190                 195                 200 tcc cag ggt ggg cag gga ttc gcc att ccg atc ggg cag gcg atg gcg           832
Ser Gln Gly Gly Gln Gly Phe Ala Ile Pro Ile Gly Gln Ala Met Ala
                205                 210                 215 atc gcg ggc cag atc cga tcg ggt ggg ggg tca ccc acc gtt cat atc           880
Ile Ala Gly Gln Ile Arg Ser Gly Gly Gly Ser Pro Thr Val His Ile
            220                 225                 230 ggg cct acc gcc ttc ctc ggc ttg ggt gtt gtc gac aac aac ggc aac           928
Gly Pro Thr Ala Phe Leu Gly Leu Gly Val Val Asp Asn Asn Gly Asn
        235                 240                 245
```

-continued

| | |
|---|---|
| ggc gca cga gtc caa cgc gtg gtc ggg agc gct ccg gcg gca agt ctc<br>Gly Ala Arg Val Gln Arg Val Val Gly Ser Ala Pro Ala Ala Ser Leu<br>250                            255                        260 | 976 |
| ggc atc tcc acc ggc gac gtg atc acc gcg gtc gac ggc gct ccg atc<br>Gly Ile Ser Thr Gly Asp Val Ile Thr Ala Val Asp Gly Ala Pro Ile<br>265                            270                        275                        280 | 1024 |
| aac tcg gcc acc gcg atg gcg gac gcg ctt aac ggg cat cat ccc ggt<br>Asn Ser Ala Thr Ala Met Ala Asp Ala Leu Asn Gly His His Pro Gly<br>                       285                        290                        295 | 1072 |
| gac gtc atc tcg gtg acc tgg caa acc aag tcg ggc ggc acg cgt aca<br>Asp Val Ile Ser Val Thr Trp Gln Thr Lys Ser Gly Gly Thr Arg Thr<br>300                            305                        310 | 1120 |
| ggg aac gtg aca ttg gcc gag gga ccc ccg gcc tga tttcgtcgcg<br>Gly Asn Val Thr Leu Ala Glu Gly Pro Pro Ala<br>                       315                        320 | 1166 |
| gataccaccc gccggccggc caattggatt ggcgccagcc gtgattgccg cgtgagcccc | 1226 |
| cgagttccgt ctcccgtgcg cgtggcatcg tggaagcaat gaacgaggca gaacacagcg | 1286 |
| tcgagcaccc tcccgtgcag ggcagtcacg tcgaaggcgg tgtggtcgag catccggatg | 1346 |
| ccaaggactt cggcagcgcc gccgccctgc ccgccgatcc gacctggttt aagcacgccg | 1406 |
| tcttctacga ggtgctggtc cgggcgttct tcgacgccag cgcggacggt tccggcgatc | 1466 |
| tgcgtggact catcgatcgc ctcgactacc tgcagtggct tggcatcgac tgcatctggt | 1526 |
| tgccgccgtt ctacgactcg ccgctgcgcg acggcggtta cgacattcgc gacttctaca | 1586 |
| aggtgctgcc cgaattcggc accgtcgacg atttcgtcgc cctggtcgac gccgctcacc | 1646 |
| ggcgaggtat ccgcatcatc accgacctgg tgatgaatca cacctcggag tcgcacccct | 1706 |
| ggtttcagga gtcccgccgc gacccagacg accgtacgg tgactattac gtgtggagcg | 1766 |
| acaccagcga gcgctacacc gacgcccgga tcatcttcgt cgacaccgaa gagtcgaact | 1826 |
| ggtcattcga tcctgtccgc cgacagttct actggcaccg attctt | 1872 |

<210> SEQ ID NO 2
<211> LENGTH: 355
<212> TYPE: PRT
<213> ORGANISM: Mycobacterium tuberculosis
<220> FEATURE:
<223> OTHER INFORMATION: 32 KD serine protease MTB32A

<400> SEQUENCE: 2

Met Ser Asn Ser Arg Arg Arg Ser Leu Arg Trp Ser Trp Leu Leu Ser
1               5                   10                  15

Val Leu Ala Ala Val Gly Leu Gly Leu Ala Thr Ala Pro Ala Gln Ala
            20                  25                  30

Ala Pro Pro Ala Leu Ser Gln Asp Arg Phe Ala Asp Phe Pro Ala Leu
        35                  40                  45

Pro Leu Asp Pro Ser Ala Met Val Ala Gln Val Gly Pro Gln Val Val
    50                  55                  60

Asn Ile Asn Thr Lys Leu Gly Tyr Asn Asn Ala Val Gly Ala Gly Thr
65                  70                  75                  80

Gly Ile Val Ile Asp Pro Asn Gly Val Val Leu Thr Asn Asn His Val
                85                  90                  95

Ile Ala Gly Ala Thr Asp Ile Asn Ala Phe Ser Val Gly Ser Gly Gln
            100                 105                 110

Thr Tyr Gly Val Asp Val Val Gly Tyr Asp Arg Thr Gln Asp Val Ala
        115                 120                 125

-continued

```
Val Leu Gln Leu Arg Gly Ala Gly Gly Leu Pro Ser Ala Ala Ile Gly
    130                 135                 140
Gly Gly Val Ala Val Gly Glu Pro Val Val Ala Met Gly Asn Ser Gly
145                 150                 155                 160
Gly Gln Gly Gly Thr Pro Arg Ala Val Pro Gly Arg Val Val Ala Leu
                165                 170                 175
Gly Gln Thr Val Gln Ala Ser Asp Ser Leu Thr Gly Ala Glu Glu Thr
            180                 185                 190
Leu Asn Gly Leu Ile Gln Phe Asp Ala Ala Ile Gln Pro Gly Asp Ser
            195                 200                 205
Gly Gly Pro Val Val Asn Gly Leu Gly Gln Val Val Gly Met Asn Thr
    210                 215                 220
Ala Ala Ser Asp Asn Phe Gln Leu Ser Gln Gly Gly Gln Gly Phe Ala
225                 230                 235                 240
Ile Pro Ile Gly Gln Ala Met Ala Ile Ala Gly Gln Ile Arg Ser Gly
                245                 250                 255
Gly Gly Ser Pro Thr Val His Ile Gly Pro Thr Ala Phe Leu Gly Leu
            260                 265                 270
Gly Val Val Asp Asn Asn Gly Asn Gly Ala Arg Val Gln Arg Val Val
    275                 280                 285
Gly Ser Ala Pro Ala Ala Ser Leu Gly Ile Ser Thr Gly Asp Val Ile
    290                 295                 300
Thr Ala Val Asp Gly Ala Pro Ile Asn Ser Ala Thr Ala Met Ala Asp
305                 310                 315                 320
Ala Leu Asn Gly His His Pro Gly Asp Val Ile Ser Val Thr Trp Gln
                325                 330                 335
Thr Lys Ser Gly Gly Thr Arg Thr Gly Asn Val Thr Leu Ala Glu Gly
            340                 345                 350
Pro Pro Ala
        355

<210> SEQ ID NO 3
<211> LENGTH: 396
<212> TYPE: DNA
<213> ORGANISM: Mycobacterium tuberculosis
<220> FEATURE:
<223> OTHER INFORMATION: 14 KD C-terminal fragment of MTB32A Ra12
<220> FEATURE:
<221> NAME/KEY: CDS
<222> LOCATION: (1)..(396)
<223> OTHER INFORMATION: Ra12

<400> SEQUENCE: 3 acg gcc gcg tcc gat aac ttc cag ctg tcc cag ggt ggg cag gga ttc      48
Thr Ala Ala Ser Asp Asn Phe Gln Leu Ser Gln Gly Gly Gln Gly Phe
  1               5                  10                  15 gcc att ccg atc ggg cag gcg atg gcg atc gcg ggc cag atc cga tcg      96
Ala Ile Pro Ile Gly Gln Ala Met Ala Ile Ala Gly Gln Ile Arg Ser
             20                  25                  30 ggt ggg ggg tca ccc acc gtt cat atc ggg cct acc gcc ttc ctc ggc     144
Gly Gly Gly Ser Pro Thr Val His Ile Gly Pro Thr Ala Phe Leu Gly
         35                  40                  45 ttg ggt gtt gtc gac aac aac ggc aac ggc gca cga gtc caa cgc gtg     192
Leu Gly Val Val Asp Asn Asn Gly Asn Gly Ala Arg Val Gln Arg Val
     50                  55                  60 gtc ggg agc gct ccg gcg gca agt ctc ggc atc tcc acc ggc gac gtg     240
Val Gly Ser Ala Pro Ala Ala Ser Leu Gly Ile Ser Thr Gly Asp Val
 65                  70                  75                  80
```

```
atc acc gcg gtc gac ggc gct ccg atc aac tcg gcc acc gcg atg gcg      288
Ile Thr Ala Val Asp Gly Ala Pro Ile Asn Ser Ala Thr Ala Met Ala
             85                  90                  95 gac gcg ctt aac ggg cat cat ccc ggt gac gtc atc tcg gtg acc tgg      336
Asp Ala Leu Asn Gly His His Pro Gly Asp Val Ile Ser Val Thr Trp
        100                 105                 110 caa acc aag tcg ggc ggc acg cgt aca ggg aac gtg aca ttg gcc gag      384
Gln Thr Lys Ser Gly Gly Thr Arg Thr Gly Asn Val Thr Leu Ala Glu
            115                 120                 125 gga ccc ccg gcc                                                       396
Gly Pro Pro Ala
    130

<210> SEQ ID NO 4
<211> LENGTH: 132
<212> TYPE: PRT
<213> ORGANISM: Mycobacterium tuberculosis
<220> FEATURE:
<223> OTHER INFORMATION: 14 KD C-terminal fragment of MTB32A Ra12

<400> SEQUENCE: 4

Thr Ala Ala Ser Asp Asn Phe Gln Leu Ser Gln Gly Gly Gln Gly Phe
 1               5                  10                  15

Ala Ile Pro Ile Gly Gln Ala Met Ala Ile Ala Gly Gln Ile Arg Ser
            20                  25                  30

Gly Gly Gly Ser Pro Thr Val His Ile Gly Pro Thr Ala Phe Leu Gly
        35                  40                  45

Leu Gly Val Val Asp Asn Asn Gly Asn Gly Ala Arg Val Gln Arg Val
    50                  55                  60

Val Gly Ser Ala Pro Ala Ala Ser Leu Gly Ile Ser Thr Gly Asp Val
65                  70                  75                  80

Ile Thr Ala Val Asp Gly Ala Pro Ile Asn Ser Ala Thr Ala Met Ala
             85                  90                  95

Asp Ala Leu Asn Gly His His Pro Gly Asp Val Ile Ser Val Thr Trp
        100                 105                 110

Gln Thr Lys Ser Gly Gly Thr Arg Thr Gly Asn Val Thr Leu Ala Glu
    115                 120                 125

Gly Pro Pro Ala
    130

<210> SEQ ID NO 5
<211> LENGTH: 702
<212> TYPE: DNA
<213> ORGANISM: Artificial Sequence
<220> FEATURE:
<223> OTHER INFORMATION: Description of Artificial Sequence:Ra12-DPPD
      fusion polypeptide
<220> FEATURE:
<221> NAME/KEY: CDS
<222> LOCATION: (4)..(696)
<223> OTHER INFORMATION: Ra12-DPPD fusion polypeptide

<400> SEQUENCE: 5 cat atg cat cac cat cac cat cac acg gcc gcg tcc gat aac ttc cag       48
    Met His His His His His His Thr Ala Ala Ser Asp Asn Phe Gln
     1               5                  10                  15 ctg tcc cag ggt ggg cag gga ttc gcc att ccg atc ggg cag gcg atg       96
Leu Ser Gln Gly Gly Gln Gly Phe Ala Ile Pro Ile Gly Gln Ala Met
            20                  25                  30 gcg atc gcg ggc cag atc cga tcg ggt ggg ggg tca ccc acc gtt cat      144
Ala Ile Ala Gly Gln Ile Arg Ser Gly Gly Gly Ser Pro Thr Val His
        35                  40                  45
```

```
atc ggg cct acc gcc ttc ctc ggc ttg ggt gtt gtc gac aac aac ggc      192
Ile Gly Pro Thr Ala Phe Leu Gly Leu Gly Val Val Asp Asn Asn Gly
    50                  55                  60 aac ggc gca cga gtc caa cgc gtg gtc ggg agc gct ccg gcg gca agt      240
Asn Gly Ala Arg Val Gln Arg Val Val Gly Ser Ala Pro Ala Ala Ser
65                  70                  75 ctc ggc atc tcc acc ggc gac gtg atc acc gcg gtc gac ggc gct ccg      288
Leu Gly Ile Ser Thr Gly Asp Val Ile Thr Ala Val Asp Gly Ala Pro
80                  85                  90                  95 atc aac tcg gcc acc gcg atg gcg gac gcg ctt aac ggg cat cat ccc      336
Ile Asn Ser Ala Thr Ala Met Ala Asp Ala Leu Asn Gly His His Pro
                100                 105                 110 ggt gac gtc atc tcg gtg acc tgg caa acc aag tcg ggc ggc acg cgt      384
Gly Asp Val Ile Ser Val Thr Trp Gln Thr Lys Ser Gly Gly Thr Arg
            115                 120                 125 aca ggg aac gtg aca ttg gcc gag gga ccc ccg gcc gaa ttc gac gac      432
Thr Gly Asn Val Thr Leu Ala Glu Gly Pro Pro Ala Glu Phe Asp Asp
        130                 135                 140 gac gac aag gat cca cct gac ccg cat cag ccg gac atg acg aaa ggc      480
Asp Asp Lys Asp Pro Pro Asp Pro His Gln Pro Asp Met Thr Lys Gly
145                 150                 155 tat tgc ccg ggt ggc cga tgg ggt ttt ggc gac ttg gcc gtg tgc gac      528
Tyr Cys Pro Gly Gly Arg Trp Gly Phe Gly Asp Leu Ala Val Cys Asp
160                 165                 170                 175 ggc gag aag tac ccc gac ggc tcg ttt tgg cac cag tgg atg caa acg      576
Gly Glu Lys Tyr Pro Asp Gly Ser Phe Trp His Gln Trp Met Gln Thr
                180                 185                 190 tgg ttt acc ggc cca cag ttt tac ttc gat tgt gtc agc ggc ggt gag      624
Trp Phe Thr Gly Pro Gln Phe Tyr Phe Asp Cys Val Ser Gly Gly Glu
            195                 200                 205 ccc ctc ccc ggc ccg ccg cca ccg ggt ggt tgc ggt ggg gca att ccg      672
Pro Leu Pro Gly Pro Pro Pro Pro Gly Gly Cys Gly Gly Ala Ile Pro
        210                 215                 220 tcc gag cag ccc aac gct ccc tga gaattc                               702
Ser Glu Gln Pro Asn Ala Pro
    225                 230

<210> SEQ ID NO 6
<211> LENGTH: 230
<212> TYPE: PRT
<213> ORGANISM: Artificial Sequence
<220> FEATURE:
<223> OTHER INFORMATION: Description of Artificial Sequence:Ra12-DPPD
      fusion polypeptide

<400> SEQUENCE: 6

Met His His His His His Thr Ala Ala Ser Asp Asn Phe Gln Leu
1               5                   10                  15

Ser Gln Gly Gly Gln Gly Phe Ala Ile Pro Ile Gly Gln Ala Met Ala
                20                  25                  30

Ile Ala Gly Gln Ile Arg Ser Gly Gly Ser Pro Thr Val His Ile
            35                  40                  45

Gly Pro Thr Ala Phe Leu Gly Leu Gly Val Val Asp Asn Asn Gly Asn
        50                  55                  60

Gly Ala Arg Val Gln Arg Val Val Gly Ser Ala Pro Ala Ala Ser Leu
65                  70                  75                  80

Gly Ile Ser Thr Gly Asp Val Ile Thr Ala Val Asp Gly Ala Pro Ile
                85                  90                  95

Asn Ser Ala Thr Ala Met Ala Asp Ala Leu Asn Gly His His Pro Gly
```

```
                    100                 105                 110
Asp Val Ile Ser Val Thr Trp Gln Thr Lys Ser Gly Gly Thr Arg Thr
            115                 120                 125

Gly Asn Val Thr Leu Ala Glu Gly Pro Pro Ala Glu Phe Asp Asp Asp
        130                 135                 140

Asp Lys Asp Pro Pro Asp Pro His Gln Pro Asp Met Thr Lys Gly Tyr
145                 150                 155                 160

Cys Pro Gly Gly Arg Trp Gly Phe Gly Asp Leu Ala Val Cys Asp Gly
                165                 170                 175

Glu Lys Tyr Pro Asp Gly Ser Phe Trp His Gln Trp Met Gln Thr Trp
            180                 185                 190

Phe Thr Gly Pro Gln Phe Tyr Phe Asp Cys Val Ser Gly Gly Glu Pro
        195                 200                 205

Leu Pro Gly Pro Pro Pro Gly Gly Cys Gly Gly Ala Ile Pro Ser
    210                 215                 220

Glu Gln Pro Asn Ala Pro
225                 230

<210> SEQ ID NO 7
<211> LENGTH: 1746
<212> TYPE: DNA
<213> ORGANISM: Artificial Sequence
<220> FEATURE:
<223> OTHER INFORMATION: Description of Artificial Sequence:Ra12-WT1
      fusion
<220> FEATURE:
<221> NAME/KEY: CDS
<222> LOCATION: (4)..(1740)
<223> OTHER INFORMATION: Ra12-WT1 fusion polypeptide

<400> SEQUENCE: 7 cat atg cat cac cat cac cat cac acg gcc gcg tcc gat aac ttc cag        48
    Met His His His His His Thr Ala Ala Ser Asp Asn Phe Gln
     1               5                  10                  15 ctg tcc cag ggt ggg cag gga ttc gcc att ccg atc ggg cag gcg atg       96
Leu Ser Gln Gly Gly Gln Gly Phe Ala Ile Pro Ile Gly Gln Ala Met
             20                  25                  30 gcg atc gcg ggc cag atc cga tcg ggt ggg ggg tca ccc acc gtt cat      144
Ala Ile Ala Gly Gln Ile Arg Ser Gly Gly Gly Ser Pro Thr Val His
         35                  40                  45 atc ggg cct acc gcc ttc ctc ggc ttg ggt gtt gtc gac aac aac ggc      192
Ile Gly Pro Thr Ala Phe Leu Gly Leu Gly Val Val Asp Asn Asn Gly
     50                  55                  60 aac ggc gca cga gtc caa cgc gtg gtc ggg agc gct ccg gcg gca agt      240
Asn Gly Ala Arg Val Gln Arg Val Val Gly Ser Ala Pro Ala Ala Ser
 65                  70                  75 ctc ggc atc tcc acc ggc gac gtg atc acc gcg gtc gac ggc gct ccg      288
Leu Gly Ile Ser Thr Gly Asp Val Ile Thr Ala Val Asp Gly Ala Pro
 80                  85                  90                  95 atc aac tcg gcc acc gcg atg gcg gac gcg ctt aac ggg cat cat ccc      336
Ile Asn Ser Ala Thr Ala Met Ala Asp Ala Leu Asn Gly His His Pro
                100                 105                 110 ggt gac gtc atc tcg gtg acc tgg caa acc aag tcg ggc ggc acg cgt      384
Gly Asp Val Ile Ser Val Thr Trp Gln Thr Lys Ser Gly Gly Thr Arg
            115                 120                 125 aca ggg aac gtg aca ttg gcc gag gga ccc ccg gcc gaa ttc ccg ctg      432
Thr Gly Asn Val Thr Leu Ala Glu Gly Pro Pro Ala Glu Phe Pro Leu
        130                 135                 140 gtg ccg cgc ggc agc ccg atg ggc tcc gac gtt cgg gac ctg aac gca      480
Val Pro Arg Gly Ser Pro Met Gly Ser Asp Val Arg Asp Leu Asn Ala
```

```
            145                 150                 155
ctg ctg ccg gca gtt ccg tcc ctg ggt ggt ggt ggt tgc gca ctg    528
Leu Leu Pro Ala Val Pro Ser Leu Gly Gly Gly Gly Cys Ala Leu
160             165                 170                 175 ccg gtt agc ggt gca gca cag tgg gct ccg gtt ctg gac ttc gca ccg    576
Pro Val Ser Gly Ala Ala Gln Trp Ala Pro Val Leu Asp Phe Ala Pro
                180                 185                 190 ccg ggt gca tcc gca tac ggt tcc ctg ggt ggt ccg gca ccg ccg    624
Pro Gly Ala Ser Ala Tyr Gly Ser Leu Gly Gly Pro Ala Pro Pro
            195                 200                 205 gca ccg ccg ccg ccg ccg ccg ccg ccg cac tcc ttc atc aaa cag    672
Ala Pro Pro Pro Pro Pro Pro Pro Pro His Ser Phe Ile Lys Gln
        210                 215                 220 gaa ccg agc tgg ggt ggt gca gaa ccg cac gaa gaa cag tgc ctg agc    720
Glu Pro Ser Trp Gly Gly Ala Glu Pro His Glu Glu Gln Cys Leu Ser
    225                 230                 235 gca ttc acc gtt cac ttc tcc ggc cag ttc act ggc aca gcc gga gcc    768
Ala Phe Thr Val His Phe Ser Gly Gln Phe Thr Gly Thr Ala Gly Ala
240                 245                 250                 255 tgt cgc tac ggg ccc ttc ggt cct cct ccg ccc agc cag gcg tca tcc    816
Cys Arg Tyr Gly Pro Phe Gly Pro Pro Pro Pro Ser Gln Ala Ser Ser
                260                 265                 270 ggc cag gcc agg atg ttt cct aac gcg ccc tac ctg ccc agc tgc ctc    864
Gly Gln Ala Arg Met Phe Pro Asn Ala Pro Tyr Leu Pro Ser Cys Leu
            275                 280                 285 gag agc cag ccc gct att cgc aat cag ggt tac agc acg gtc acc ttc    912
Glu Ser Gln Pro Ala Ile Arg Asn Gln Gly Tyr Ser Thr Val Thr Phe
        290                 295                 300 gac ggg acg ccc agc tac ggt cac acg ccc tcg cac cat gcg gcg cag    960
Asp Gly Thr Pro Ser Tyr Gly His Thr Pro Ser His His Ala Ala Gln
305                 310                 315 ttc ccc aac cac tca ttc aag cat gag gat ccc atg ggc cag cag ggc    1008
Phe Pro Asn His Ser Phe Lys His Glu Asp Pro Met Gly Gln Gln Gly
320                 325                 330                 335 tcg ctg ggt gag cag cag tac tcg gtg ccg ccc ccg gtc tat ggc tgc    1056
Ser Leu Gly Glu Gln Gln Tyr Ser Val Pro Pro Pro Val Tyr Gly Cys
                340                 345                 350 cac acc ccc acc gac agc tgc acc ggc agc cag gct ttg ctg ctg agg    1104
His Thr Pro Thr Asp Ser Cys Thr Gly Ser Gln Ala Leu Leu Leu Arg
            355                 360                 365 acg ccc tac agc agt gac aat tta tac caa atg aca tcc cag ctt gaa    1152
Thr Pro Tyr Ser Ser Asp Asn Leu Tyr Gln Met Thr Ser Gln Leu Glu
        370                 375                 380 tgc atg acc tgg aat cag atg aac tta gga gcc acc tta aag ggc cac    1200
Cys Met Thr Trp Asn Gln Met Asn Leu Gly Ala Thr Leu Lys Gly His
385                 390                 395 agc aca ggg tac gag agc gat aac cac aca acg ccc atc ctc tgc gga    1248
Ser Thr Gly Tyr Glu Ser Asp Asn His Thr Thr Pro Ile Leu Cys Gly
400                 405                 410                 415 gcc caa tac aga ata cac acg cac ggt gtc ttc aga ggc att cag gat    1296
Ala Gln Tyr Arg Ile His Thr His Gly Val Phe Arg Gly Ile Gln Asp
                420                 425                 430 gtg cga cgt gtg cct gga gta gcc ccg act ctt gta cgg tcg gca tct    1344
Val Arg Arg Val Pro Gly Val Ala Pro Thr Leu Val Arg Ser Ala Ser
            435                 440                 445 gag acc agt gag aaa cgc ccc ttc atg tgt gct tac tca ggc tgc aat    1392
Glu Thr Ser Glu Lys Arg Pro Phe Met Cys Ala Tyr Ser Gly Cys Asn
        450                 455                 460 aag aga tat ttt aag ctg tcc cac tta cag atg cac agc agg aag cac    1440
```

-continued

```
Lys Arg Tyr Phe Lys Leu Ser His Leu Gln Met His Ser Arg Lys His
            465                 470                 475 act ggt gag aaa cca tac cag tgt gac ttc aag gac tgt gaa cga agg      1488
Thr Gly Glu Lys Pro Tyr Gln Cys Asp Phe Lys Asp Cys Glu Arg Arg
480                 485                 490                 495 ttt ttt cgt tca gac cag ctc aaa aga cac caa agg aga cat aca ggt      1536
Phe Phe Arg Ser Asp Gln Leu Lys Arg His Gln Arg Arg His Thr Gly
                500                 505                 510 gtg aaa cca ttc cag tgt aaa act tgt cag cga aag ttc tcc cgg tcc      1584
Val Lys Pro Phe Gln Cys Lys Thr Cys Gln Arg Lys Phe Ser Arg Ser
            515                 520                 525 gac cac ctg aag acc cac acc agg act cat aca ggt gaa aag ccc ttc      1632
Asp His Leu Lys Thr His Thr Arg Thr His Thr Gly Glu Lys Pro Phe
        530                 535                 540 agc tgt cgg tgg cca agt tgt cag aaa aag ttt gcc cgg tca gat gaa      1680
Ser Cys Arg Trp Pro Ser Cys Gln Lys Lys Phe Ala Arg Ser Asp Glu
    545                 550                 555 tta gtc cgc cat cac aac atg cat cag aga aac atg acc aaa ctc cag      1728
Leu Val Arg His His Asn Met His Gln Arg Asn Met Thr Lys Leu Gln
560                 565                 570                 575 ctg gcg ctt tga gaattc                                               1746
Leu Ala Leu
```

<210> SEQ ID NO 8
<211> LENGTH: 578
<212> TYPE: PRT
<213> ORGANISM: Artificial Sequence
<220> FEATURE:
<223> OTHER INFORMATION: Description of Artificial Sequence:Ra12-WT1
    fusion polypeptide

<400> SEQUENCE: 8

```
Met His His His His His Thr Ala Ala Ser Asp Asn Phe Gln Leu
  1               5                  10                  15

Ser Gln Gly Gly Gln Gly Phe Ala Ile Pro Ile Gly Gln Ala Met Ala
             20                  25                  30

Ile Ala Gly Gln Ile Arg Ser Gly Gly Ser Pro Thr Val His Ile
         35                  40                  45

Gly Pro Thr Ala Phe Leu Gly Leu Val Val Asp Asn Asn Gly Asn
     50                  55                  60

Gly Ala Arg Val Gln Arg Val Val Gly Ser Ala Pro Ala Ser Leu
 65                  70                  75                  80

Gly Ile Ser Thr Gly Asp Val Ile Thr Ala Val Asp Gly Ala Pro Ile
                 85                  90                  95

Asn Ser Ala Thr Ala Met Ala Asp Ala Leu Asn Gly His His Pro Gly
            100                 105                 110

Asp Val Ile Ser Val Thr Trp Gln Thr Lys Ser Gly Gly Thr Arg Thr
        115                 120                 125

Gly Asn Val Thr Leu Ala Glu Gly Pro Pro Ala Glu Phe Pro Leu Val
    130                 135                 140

Pro Arg Gly Ser Pro Met Gly Ser Asp Val Arg Asp Leu Asn Ala Leu
145                 150                 155                 160

Leu Pro Ala Val Pro Ser Leu Gly Gly Gly Gly Cys Ala Leu Pro
                165                 170                 175

Val Ser Gly Ala Ala Gln Trp Ala Pro Val Leu Asp Phe Ala Pro Pro
            180                 185                 190

Gly Ala Ser Ala Tyr Gly Ser Leu Gly Gly Pro Ala Pro Pro Pro Ala
        195                 200                 205
```

```
Pro Pro Pro Pro Pro Pro Pro His Ser Phe Ile Lys Gln Glu
    210             215                 220
Pro Ser Trp Gly Gly Ala Glu Pro His Glu Glu Gln Cys Leu Ser Ala
225                 230                 235                 240
Phe Thr Val His Phe Ser Gly Gln Phe Thr Gly Thr Ala Gly Ala Cys
                245                 250                 255
Arg Tyr Gly Pro Phe Gly Pro Pro Pro Ser Gln Ala Ser Ser Gly
            260                 265                 270
Gln Ala Arg Met Phe Pro Asn Ala Pro Tyr Leu Pro Ser Cys Leu Glu
        275                 280                 285
Ser Gln Pro Ala Ile Arg Asn Gln Gly Tyr Ser Thr Val Thr Phe Asp
    290                 295                 300
Gly Thr Pro Ser Tyr Gly His Thr Pro Ser His His Ala Ala Gln Phe
305                 310                 315                 320
Pro Asn His Ser Phe Lys His Glu Asp Pro Met Gly Gln Gln Gly Ser
                325                 330                 335
Leu Gly Glu Gln Gln Tyr Ser Val Pro Pro Val Tyr Gly Cys His
            340                 345                 350
Thr Pro Thr Asp Ser Cys Thr Gly Ser Gln Ala Leu Leu Leu Arg Thr
        355                 360                 365
Pro Tyr Ser Ser Asp Asn Leu Tyr Gln Met Thr Ser Gln Leu Glu Cys
    370                 375                 380
Met Thr Trp Asn Gln Met Asn Leu Gly Ala Thr Leu Lys Gly His Ser
385                 390                 395                 400
Thr Gly Tyr Glu Ser Asp Asn His Thr Thr Pro Ile Leu Cys Gly Ala
                405                 410                 415
Gln Tyr Arg Ile His Thr His Gly Val Phe Arg Gly Ile Gln Asp Val
            420                 425                 430
Arg Arg Val Pro Gly Val Ala Pro Thr Leu Val Arg Ser Ala Ser Glu
        435                 440                 445
Thr Ser Glu Lys Arg Pro Phe Met Cys Ala Tyr Ser Gly Cys Asn Lys
    450                 455                 460
Arg Tyr Phe Lys Leu Ser His Leu Gln Met His Ser Arg Lys His Thr
465                 470                 475                 480
Gly Glu Lys Pro Tyr Gln Cys Asp Phe Lys Asp Cys Glu Arg Arg Phe
                485                 490                 495
Phe Arg Ser Asp Gln Leu Lys Arg His Gln Arg Arg His Thr Gly Val
            500                 505                 510
Lys Pro Phe Gln Cys Lys Thr Cys Gln Arg Lys Phe Ser Arg Ser Asp
        515                 520                 525
His Leu Lys Thr His Thr Arg Thr His Thr Gly Glu Lys Pro Phe Ser
    530                 535                 540
Cys Arg Trp Pro Ser Cys Gln Lys Lys Phe Ala Arg Ser Asp Glu Leu
545                 550                 555                 560
Val Arg His His Asn Met His Gln Arg Asn Met Thr Lys Leu Gln Leu
                565                 570                 575
Ala Leu

<210> SEQ ID NO 9
<211> LENGTH: 672
<212> TYPE: DNA
<213> ORGANISM: Artificial Sequence
<220> FEATURE:
<223> OTHER INFORMATION: Description of Artificial Sequence:Ra12-human
``` mammaglobin fusion
<220> FEATURE:
<221> NAME/KEY: CDS
<222> LOCATION: (4)..(666)
<223> OTHER INFORMATION: Ra12-human mammaglobin fusion polypeptide

<400> SEQUENCE: 9

```
cat atg cat cac cat cac cat cac acg gcc gcg tcc gat aac ttc cag        48
    Met His His His His His His Thr Ala Ala Ser Asp Asn Phe Gln
    1               5                   10                  15 ctg tcc cag ggt ggg cag gga ttc gcc att ccg atc ggg cag gcg atg        96
Leu Ser Gln Gly Gly Gln Gly Phe Ala Ile Pro Ile Gly Gln Ala Met
                20                  25                  30 gcg atc gcg ggc cag atc cga tcg ggt ggg ggg tca ccc acc gtt cat       144
Ala Ile Ala Gly Gln Ile Arg Ser Gly Gly Gly Ser Pro Thr Val His
            35                  40                  45 atc ggg cct acc gcc ttc ctc ggc ttg ggt gtt gtc gac aac aac ggc       192
Ile Gly Pro Thr Ala Phe Leu Gly Leu Gly Val Val Asp Asn Asn Gly
        50                  55                  60 aac ggc gca cga gtc caa cgc gtg gtc ggg agc gct ccg gcg gca agt       240
Asn Gly Ala Arg Val Gln Arg Val Val Gly Ser Ala Pro Ala Ala Ser
    65                  70                  75 ctc ggc atc tcc acc ggc gac gtg atc acc gcg gtc gac ggc gct ccg       288
Leu Gly Ile Ser Thr Gly Asp Val Ile Thr Ala Val Asp Gly Ala Pro
80                  85                  90                  95 atc aac tcg gcc acc gcg atg gcg gac gcg ctt aac ggg cat cat ccc       336
Ile Asn Ser Ala Thr Ala Met Ala Asp Ala Leu Asn Gly His His Pro
                100                 105                 110 ggt gac gtc atc tcg gtg acc tgg caa acc aag tcg ggc ggc acg cgt       384
Gly Asp Val Ile Ser Val Thr Trp Gln Thr Lys Ser Gly Gly Thr Arg
            115                 120                 125 aca ggg aac gtg aca ttg gcc gag gga ccc ccg gcc gaa ttc atc gag       432
Thr Gly Asn Val Thr Leu Ala Glu Gly Pro Pro Ala Glu Phe Ile Glu
        130                 135                 140 gga agg ggc tct ggc tgc ccc tta ttg gag aat gtg att tcc aag aca       480
Gly Arg Gly Ser Gly Cys Pro Leu Leu Glu Asn Val Ile Ser Lys Thr
    145                 150                 155 atc aat cca caa gtg tct aag act gaa tac aaa gaa ctt ctt caa gag       528
Ile Asn Pro Gln Val Ser Lys Thr Glu Tyr Lys Glu Leu Leu Gln Glu
160                 165                 170                 175 ttc ata gac gac aat gcc act aca aat gcc ata gat gaa ttg aag gaa       576
Phe Ile Asp Asp Asn Ala Thr Thr Asn Ala Ile Asp Glu Leu Lys Glu
                180                 185                 190 tgt ttt ctt aac caa acg gat gaa act ctg agc aat gtt gag gtg ttt       624
Cys Phe Leu Asn Gln Thr Asp Glu Thr Leu Ser Asn Val Glu Val Phe
            195                 200                 205 atg caa tta ata tat gac agc agt ctt tgt gat tta ttt taa gaattc       672
Met Gln Leu Ile Tyr Asp Ser Ser Leu Cys Asp Leu Phe
        210                 215                 220
```

<210> SEQ ID NO 10
<211> LENGTH: 220
<212> TYPE: PRT
<213> ORGANISM: Artificial Sequence
<220> FEATURE:
<223> OTHER INFORMATION: Description of Artificial Sequence:Ra12-human
      mammaglobin fusion polypeptide

<400> SEQUENCE: 10

```
Met His His His His His His Thr Ala Ala Ser Asp Asn Phe Gln Leu
1               5                   10                  15

Ser Gln Gly Gly Gln Gly Phe Ala Ile Pro Ile Gly Gln Ala Met Ala
```

-continued

```
                 20                  25                  30
Ile Ala Gly Gln Ile Arg Ser Gly Gly Gly Ser Pro Thr Val His Ile
         35                  40                  45

Gly Pro Thr Ala Phe Leu Gly Leu Gly Val Val Asp Asn Asn Gly Asn
 50                  55                  60

Gly Ala Arg Val Gln Arg Val Val Gly Ser Ala Pro Ala Ala Ser Leu
 65                  70                  75                  80

Gly Ile Ser Thr Gly Asp Val Ile Thr Ala Val Asp Gly Ala Pro Ile
                 85                  90                  95

Asn Ser Ala Thr Ala Met Ala Asp Ala Leu Asn Gly His His Pro Gly
                100                 105                 110

Asp Val Ile Ser Val Thr Trp Gln Thr Lys Ser Gly Gly Thr Arg Thr
            115                 120                 125

Gly Asn Val Thr Leu Ala Glu Gly Pro Pro Ala Glu Phe Ile Glu Gly
        130                 135                 140

Arg Gly Ser Gly Cys Pro Leu Leu Glu Asn Val Ile Ser Lys Thr Ile
145                 150                 155                 160

Asn Pro Gln Val Ser Lys Thr Glu Tyr Lys Glu Leu Leu Gln Glu Phe
                165                 170                 175

Ile Asp Asp Asn Ala Thr Thr Asn Ala Ile Asp Glu Leu Lys Glu Cys
            180                 185                 190

Phe Leu Asn Gln Thr Asp Glu Thr Leu Ser Asn Val Glu Val Phe Met
        195                 200                 205

Gln Leu Ile Tyr Asp Ser Ser Leu Cys Asp Leu Phe
    210                 215                 220

<210> SEQ ID NO 11
<211> LENGTH: 2191
<212> TYPE: DNA
<213> ORGANISM: Artificial Sequence
<220> FEATURE:
<223> OTHER INFORMATION: Description of Artificial Sequence:Ra12-H9-32A
      fusion (Ra12-MTB39-MTB32A(N-ter) fusion)
<220> FEATURE:
<221> NAME/KEY: CDS
<222> LOCATION: (1)..(2190)
<223> OTHER INFORMATION: Ra12-H9-32A (Ra12-MTB39-MTB32A(N-ter)) fusion
      polypeptide

<400> SEQUENCE: 11 atg cat cac cat cac cat cac acg gcc gcg tcc gat aac ttc cag ctg      48
Met His His His His His His Thr Ala Ala Ser Asp Asn Phe Gln Leu
  1               5                  10                  15 tcc cag ggt ggg cag gga ttc gcc att ccg atc ggg cag gcg atg gcg      96
Ser Gln Gly Gly Gln Gly Phe Ala Ile Pro Ile Gly Gln Ala Met Ala
             20                  25                  30 atc gcg ggc cag atc cga tcg ggt ggg ggg tca ccc acc gtt cat atc     144
Ile Ala Gly Gln Ile Arg Ser Gly Gly Gly Ser Pro Thr Val His Ile
         35                  40                  45 ggg cct acc gcc ttc ctc ggc ttg ggt gtt gtc gac aac aac ggc aac     192
Gly Pro Thr Ala Phe Leu Gly Leu Gly Val Val Asp Asn Asn Gly Asn
 50                  55                  60 ggc gca cga gtc caa cgc gtg gtc ggg agc gct ccg gcg gca agt ctc     240
Gly Ala Arg Val Gln Arg Val Val Gly Ser Ala Pro Ala Ala Ser Leu
 65                  70                  75                  80 ggc atc tcc acc ggc gac gtg atc acc gcg gtc gac ggc gct ccg atc     288
Gly Ile Ser Thr Gly Asp Val Ile Thr Ala Val Asp Gly Ala Pro Ile
                 85                  90                  95 aac tcg gcc acc gcg atg gcg gac gcg ctt aac ggg cat cat ccc ggt     336
```

```
                                                                -continued

Asn Ser Ala Thr Ala Met Ala Asp Ala Leu Asn Gly His His Pro Gly
            100                 105                 110 gac gtc atc tcg gtg acc tgg caa acc aag tcg ggc ggc acg cgt aca           384
Asp Val Ile Ser Val Thr Trp Gln Thr Lys Ser Gly Gly Thr Arg Thr
            115                 120                 125 ggg aac gtg aca ttg gcc gag gga ccc ccg gcc gaa ttc atg gtg gat           432
Gly Asn Val Thr Leu Ala Glu Gly Pro Pro Ala Glu Phe Met Val Asp
130                 135                 140 ttc ggg gcg tta cca ccg gag atc aac tcc gcg agg atg tac gcc ggc           480
Phe Gly Ala Leu Pro Pro Glu Ile Asn Ser Ala Arg Met Tyr Ala Gly
145                 150                 155                 160 ccg ggt tcg gcc tcg ctg gtg gcc gcg gct cag atg tgg gac agc gtg           528
Pro Gly Ser Ala Ser Leu Val Ala Ala Ala Gln Met Trp Asp Ser Val
                165                 170                 175 gcg agt gac ctg ttt tcg gcc gcg tcg gcg ttt cag tcg gtg gtc tgg           576
Ala Ser Asp Leu Phe Ser Ala Ala Ser Ala Phe Gln Ser Val Val Trp
            180                 185                 190 ggt ctg acg gtg ggg tcg tgg ata ggt tcg tcg gcg ggt ctg atg gtg           624
Gly Leu Thr Val Gly Ser Trp Ile Gly Ser Ser Ala Gly Leu Met Val
        195                 200                 205 gcg gcg gcc tcg ccg tat gtg gcg tgg atg agc gtc acc gcg ggg cag           672
Ala Ala Ala Ser Pro Tyr Val Ala Trp Met Ser Val Thr Ala Gly Gln
    210                 215                 220 gcc gag ctg acc gcc gcc cag gtc cgg gtt gct gcg gcg gcc tac gag           720
Ala Glu Leu Thr Ala Ala Gln Val Arg Val Ala Ala Ala Ala Tyr Glu
225                 230                 235                 240 acg gcg tat ggg ctg acg gtg ccc ccg ccg gtg atc gcc gag aac cgt           768
Thr Ala Tyr Gly Leu Thr Val Pro Pro Pro Val Ile Ala Glu Asn Arg
                245                 250                 255 gct gaa ctg atg att ctg ata gcg acc aac ctc ttg ggg caa aac acc           816
Ala Glu Leu Met Ile Leu Ile Ala Thr Asn Leu Leu Gly Gln Asn Thr
            260                 265                 270 ccg gcg atc gcg gtc aac gag gcc gaa tac ggc gag atg tgg gcc caa           864
Pro Ala Ile Ala Val Asn Glu Ala Glu Tyr Gly Glu Met Trp Ala Gln
        275                 280                 285 gac gcc gcc gcg atg ttt ggc tac gcc gcg gcg acg gcg acg gcg acg           912
Asp Ala Ala Ala Met Phe Gly Tyr Ala Ala Ala Thr Ala Thr Ala Thr
    290                 295                 300 gcg acg ttg ctg ccg ttc gag gag gcg ccg gag atg acc agc gcg ggt           960
Ala Thr Leu Leu Pro Phe Glu Glu Ala Pro Glu Met Thr Ser Ala Gly
305                 310                 315                 320 ggg ctc ctc gag cag gcc gcc gcg gtc gag gag gcc tcc gac acc gcc          1008
Gly Leu Leu Glu Gln Ala Ala Ala Val Glu Glu Ala Ser Asp Thr Ala
                325                 330                 335 gcg gcg aac cag ttg atg aac aat gtg ccc cag gcg ctg caa cag ctg          1056
Ala Ala Asn Gln Leu Met Asn Asn Val Pro Gln Ala Leu Gln Gln Leu
            340                 345                 350 gcc cag ccc acg cag ggc acc acg cct tct tcc aag ctg ggt ggc ctg          1104
Ala Gln Pro Thr Gln Gly Thr Thr Pro Ser Ser Lys Leu Gly Gly Leu
        355                 360                 365 tgg aag acg gtc tcg ccg cat cgg tcg ccg atc agc aac atg gtg tcg          1152
Trp Lys Thr Val Ser Pro His Arg Ser Pro Ile Ser Asn Met Val Ser
    370                 375                 380 atg gcc aac aac cac atg tcg atg acc aac tcg ggt gtg tcg atg acc          1200
Met Ala Asn Asn His Met Ser Met Thr Asn Ser Gly Val Ser Met Thr
385                 390                 395                 400 aac acc ttg agc tcg atg ttg aag ggc ttt gct ccg gcg gcg gcc gcc          1248
Asn Thr Leu Ser Ser Met Leu Lys Gly Phe Ala Pro Ala Ala Ala Ala
                405                 410                 415
```

```
cag gcc gtg caa acc gcg gcg caa aac ggg gtc cgg gcg atg agc tcg    1296
Gln Ala Val Gln Thr Ala Ala Gln Asn Gly Val Arg Ala Met Ser Ser
            420                 425                 430 ctg ggc agc tcg ctg ggt tct tcg ggt ctg ggc ggt ggg gtg gcc gcc    1344
Leu Gly Ser Ser Leu Gly Ser Ser Gly Leu Gly Gly Gly Val Ala Ala
        435                 440                 445 aac ttg ggt cgg gcg gcc tcg gtc ggt tcg ttg tcg gtg ccg cag gcc    1392
Asn Leu Gly Arg Ala Ala Ser Val Gly Ser Leu Ser Val Pro Gln Ala
450                 455                 460 tgg gcc gcg gcc aac cag gca gtc acc ccg gcg gcg cgg gcg ctg ccg    1440
Trp Ala Ala Ala Asn Gln Ala Val Thr Pro Ala Ala Arg Ala Leu Pro
465                 470                 475                 480 ctg acc agc ctg acc agc gcc gcg gaa aga ggg ccc ggg cag atg ctg    1488
Leu Thr Ser Leu Thr Ser Ala Ala Glu Arg Gly Pro Gly Gln Met Leu
                485                 490                 495 ggc ggg ctg ccg gtg ggg cag atg ggc gcc agg gcc ggt ggt ggg ctc    1536
Gly Gly Leu Pro Val Gly Gln Met Gly Ala Arg Ala Gly Gly Gly Leu
            500                 505                 510 agt ggt gtg ctg cgt gtt ccg ccg cga ccc tat gtg atg ccg cat tct    1584
Ser Gly Val Leu Arg Val Pro Pro Arg Pro Tyr Val Met Pro His Ser
        515                 520                 525 ccg gca gcc ggc gat atc gcc ccg ccg gcc ttg tcg cag gac cgg ttc    1632
Pro Ala Ala Gly Asp Ile Ala Pro Pro Ala Leu Ser Gln Asp Arg Phe
530                 535                 540 gcc gac ttc ccc gcg ctg ccc ctc gac ccg tcc gcg atg gtc gcc caa    1680
Ala Asp Phe Pro Ala Leu Pro Leu Asp Pro Ser Ala Met Val Ala Gln
545                 550                 555                 560 gtg ggg cca cag gtg gtc aac atc aac acc aaa ctg ggc tac aac aac    1728
Val Gly Pro Gln Val Val Asn Ile Asn Thr Lys Leu Gly Tyr Asn Asn
                565                 570                 575 gcc gtg ggc gcc ggg acc ggc atc gtc atc gat ccc aac ggt gtc gtg    1776
Ala Val Gly Ala Gly Thr Gly Ile Val Ile Asp Pro Asn Gly Val Val
            580                 585                 590 ctg acc aac aac cac gtg atc gcg ggc gcc acc gac atc aat gcg ttc    1824
Leu Thr Asn Asn His Val Ile Ala Gly Ala Thr Asp Ile Asn Ala Phe
        595                 600                 605 agc gtc ggc tcc ggc caa acc tac ggc gtc gat gtg gtc ggg tat gac    1872
Ser Val Gly Ser Gly Gln Thr Tyr Gly Val Asp Val Val Gly Tyr Asp
610                 615                 620 cgc acc cag gat gtc gcg gtg ctg cag ctg cgc ggt gcc ggt ggc ctg    1920
Arg Thr Gln Asp Val Ala Val Leu Gln Leu Arg Gly Ala Gly Gly Leu
625                 630                 635                 640 ccg tcg gcg gcg atc ggt ggc ggc gtc gcg gtt ggt gag ccc gtc gtc    1968
Pro Ser Ala Ala Ile Gly Gly Gly Val Ala Val Gly Glu Pro Val Val
                645                 650                 655 gcg atg ggc aac agc ggt ggg cag ggc gga acg ccc cgt gcg gtg cct    2016
Ala Met Gly Asn Ser Gly Gly Gln Gly Gly Thr Pro Arg Ala Val Pro
            660                 665                 670 ggc agg gtg gtc gcg ctc ggc caa acc gtg cag gcg tcg gat tcg ctg    2064
Gly Arg Val Val Ala Leu Gly Gln Thr Val Gln Ala Ser Asp Ser Leu
        675                 680                 685 acc ggt gcc gaa gag aca ttg aac ggg ttg atc cag ttc gat gcc gcg    2112
Thr Gly Ala Glu Glu Thr Leu Asn Gly Leu Ile Gln Phe Asp Ala Ala
690                 695                 700 atc cag ccc ggt gat tcg ggc ggg ccc gtc gtc aac ggc cta gga cag    2160
Ile Gln Pro Gly Asp Ser Gly Gly Pro Val Val Asn Gly Leu Gly Gln
705                 710                 715                 720 gtg gtc ggt atg aac acg gcc gcg tcc tag g                          2191
Val Val Gly Met Asn Thr Ala Ala Ser
                725                 730
```

<210> SEQ ID NO 12
<211> LENGTH: 729
<212> TYPE: PRT
<213> ORGANISM: Artificial Sequence
<220> FEATURE:
<223> OTHER INFORMATION: Description of Artificial Sequence:Ra12-H9-32A
    fusion polypeptide (Ra12-MTB39-MTB32A(N-ter) fusion polypeptide)

<400> SEQUENCE: 12

```
Met His His His His His Thr Ala Ala Ser Asp Asn Phe Gln Leu
 1               5                  10                  15

Ser Gln Gly Gly Gln Gly Phe Ala Ile Pro Ile Gly Gln Ala Met Ala
                20                  25                  30

Ile Ala Gly Gln Ile Arg Ser Gly Gly Ser Pro Thr Val His Ile
            35                  40                  45

Gly Pro Thr Ala Phe Leu Gly Leu Gly Val Val Asp Asn Asn Gly Asn
        50                  55                  60

Gly Ala Arg Val Gln Arg Val Val Gly Ser Ala Pro Ala Ser Leu
65                  70                  75                  80

Gly Ile Ser Thr Gly Asp Val Ile Thr Ala Val Asp Gly Ala Pro Ile
                85                  90                  95

Asn Ser Ala Thr Ala Met Ala Asp Ala Leu Asn Gly His His Pro Gly
            100                 105                 110

Asp Val Ile Ser Val Thr Trp Gln Thr Lys Ser Gly Gly Thr Arg Thr
        115                 120                 125

Gly Asn Val Thr Leu Ala Glu Gly Pro Pro Ala Glu Phe Met Val Asp
    130                 135                 140

Phe Gly Ala Leu Pro Pro Glu Ile Asn Ser Ala Arg Met Tyr Ala Gly
145                 150                 155                 160

Pro Gly Ser Ala Ser Leu Val Ala Ala Ala Gln Met Trp Asp Ser Val
                165                 170                 175

Ala Ser Asp Leu Phe Ser Ala Ala Ser Ala Phe Gln Ser Val Val Trp
            180                 185                 190

Gly Leu Thr Val Gly Ser Trp Ile Gly Ser Ser Ala Gly Leu Met Val
        195                 200                 205

Ala Ala Ala Ser Pro Tyr Val Ala Trp Met Ser Val Thr Ala Gly Gln
    210                 215                 220

Ala Glu Leu Thr Ala Ala Gln Val Arg Val Ala Ala Ala Tyr Glu
225                 230                 235                 240

Thr Ala Tyr Gly Leu Thr Val Pro Pro Pro Val Ile Ala Glu Asn Arg
                245                 250                 255

Ala Glu Leu Met Ile Leu Ile Ala Thr Asn Leu Leu Gly Gln Asn Thr
            260                 265                 270

Pro Ala Ile Ala Val Asn Glu Ala Glu Tyr Gly Glu Met Trp Ala Gln
        275                 280                 285

Asp Ala Ala Ala Met Phe Gly Tyr Ala Ala Ala Thr Ala Thr Ala Thr
    290                 295                 300

Ala Thr Leu Leu Pro Phe Glu Glu Ala Pro Glu Met Thr Ser Ala Gly
305                 310                 315                 320

Gly Leu Leu Glu Gln Ala Ala Val Glu Glu Ala Ser Asp Thr Ala
                325                 330                 335

Ala Ala Asn Gln Leu Met Asn Asn Val Pro Gln Ala Leu Gln Gln Leu
            340                 345                 350

Ala Gln Pro Thr Gln Gly Thr Thr Pro Ser Ser Lys Leu Gly Gly Leu
```

```
                    355                 360                 365
Trp Lys Thr Val Ser Pro His Arg Ser Pro Ile Ser Asn Met Val Ser
370                 375                 380

Met Ala Asn Asn His Met Ser Met Thr Asn Ser Gly Val Ser Met Thr
385                 390                 395                 400

Asn Thr Leu Ser Ser Met Leu Lys Gly Phe Ala Pro Ala Ala Ala Ala
                405                 410                 415

Gln Ala Val Gln Thr Ala Ala Gln Asn Gly Val Arg Ala Met Ser Ser
            420                 425                 430

Leu Gly Ser Ser Leu Gly Ser Ser Gly Leu Gly Gly Val Ala Ala
        435                 440                 445

Asn Leu Gly Arg Ala Ala Ser Val Gly Ser Leu Ser Val Pro Gln Ala
450                 455                 460

Trp Ala Ala Ala Asn Gln Ala Val Thr Pro Ala Ala Arg Ala Leu Pro
465                 470                 475                 480

Leu Thr Ser Leu Thr Ser Ala Ala Glu Arg Gly Pro Gly Gln Met Leu
                485                 490                 495

Gly Gly Leu Pro Val Gly Gln Met Gly Ala Arg Ala Gly Gly Gly Leu
            500                 505                 510

Ser Gly Val Leu Arg Val Pro Pro Arg Pro Tyr Val Met Pro His Ser
        515                 520                 525

Pro Ala Ala Gly Asp Ile Ala Pro Pro Ala Leu Ser Gln Asp Arg Phe
530                 535                 540

Ala Asp Phe Pro Ala Leu Pro Leu Asp Pro Ser Ala Met Val Ala Gln
545                 550                 555                 560

Val Gly Pro Gln Val Val Asn Ile Asn Thr Lys Leu Gly Tyr Asn Asn
                565                 570                 575

Ala Val Gly Ala Gly Thr Gly Ile Val Ile Asp Pro Asn Gly Val Val
            580                 585                 590

Leu Thr Asn Asn His Val Ile Ala Gly Ala Thr Asp Ile Asn Ala Phe
        595                 600                 605

Ser Val Gly Ser Gly Gln Thr Tyr Gly Val Asp Val Val Gly Tyr Asp
610                 615                 620

Arg Thr Gln Asp Val Ala Val Leu Gln Leu Arg Gly Ala Gly Gly Leu
625                 630                 635                 640

Pro Ser Ala Ala Ile Gly Gly Val Ala Val Gly Glu Pro Val Val
                645                 650                 655

Ala Met Gly Asn Ser Gly Gly Gln Gly Gly Thr Pro Arg Ala Val Pro
            660                 665                 670

Gly Arg Val Val Ala Leu Gly Gln Thr Val Gln Ala Ser Asp Ser Leu
        675                 680                 685

Thr Gly Ala Glu Glu Thr Leu Asn Gly Leu Ile Gln Phe Asp Ala Ala
690                 695                 700

Ile Gln Pro Gly Asp Ser Gly Pro Val Val Asn Gly Leu Gly Gln
705                 710                 715                 720

Val Val Gly Met Asn Thr Ala Ala Ser
                725

<210> SEQ ID NO 13
<211> LENGTH: 51
<212> TYPE: DNA
<213> ORGANISM: Artificial Sequence
<220> FEATURE:
<223> OTHER INFORMATION: Description of Artificial Sequence:
      oligonucleotide primer for PCR amplification of Ra12 C-terminal
```

-continued fragment of MTB32A

<400> SEQUENCE: 13
caattacata tgcatcacca tcaccatcac acggccgcgt ccgataactt c        51

<210> SEQ ID NO 14
<211> LENGTH: 33
<212> TYPE: DNA
<213> ORGANISM: Artificial Sequence
<220> FEATURE:
<223> OTHER INFORMATION: Description of Artificial Sequence:3'
      oligonucleotide primer for PCR amplification of
      Ra12 C-terminal fragment of MTB32A

<400> SEQUENCE: 14
ctaatcgaat tcggccgggg gtccctcggc caa        33

<210> SEQ ID NO 15
<211> LENGTH: 48
<212> TYPE: DNA
<213> ORGANISM: Artificial Sequence
<220> FEATURE:
<223> OTHER INFORMATION: Description of Artificial Sequence:5'
      oligonucleotide primer containing enterokinase
      recognition site for PCR amplification of DPPD
      mature secreted form

<400> SEQUENCE: 15
caattagaat tcgacgacga cgacaaggat ccacctgacc cgcatcag        48

<210> SEQ ID NO 16
<211> LENGTH: 33
<212> TYPE: DNA
<213> ORGANISM: Artificial Sequence
<220> FEATURE:
<223> OTHER INFORMATION: Description of Artificial Sequence:3'
      oligonucleotide primer containing enterokinase
      recognition site for PCR amplification of DPPD
      mature secreted form

<400> SEQUENCE: 16
caattagaat tctcagggag cgttgggctg ctc        33

<210> SEQ ID NO 17
<211> LENGTH: 30
<212> TYPE: PRT
<213> ORGANISM: Artificial Sequence
<220> FEATURE:
<223> OTHER INFORMATION: Description of Artificial Sequence:Ra12(short)
      polypeptide

<400> SEQUENCE: 17

Thr Ala Ala Ser Asp Asn Phe Gln Leu Ser Gln Gly Gly Gln Gly Phe
 1               5                  10                  15

Ala Ile Pro Ile Gly Gln Ala Met Ala Ile Ala Gly Gln Ile
            20                  25                  30

<210> SEQ ID NO 18
<211> LENGTH: 128
<212> TYPE: PRT
<213> ORGANISM: Artificial Sequence
<220> FEATURE:
<223> OTHER INFORMATION: Description of Artificial Sequence:Ra12(long)
      polypeptide

<400> SEQUENCE: 18

Thr Ala Ala Ser Asp Asn Phe Gln Leu Ser Gln Gly Gly Gln Gly Phe

-continued

```
                1               5                  10                 15
            Ala Ile Pro Ile Gly Gln Ala Met Ala Ile Ala Gly Gln Ile Lys Leu
                        20                  25                  30

Pro Thr Val His Ile Gly Pro Thr Ala Phe Leu Gly Leu Gly Val Val
                        35                  40                  45

Asp Asn Asn Gly Asn Gly Ala Arg Val Gln Arg Val Val Gly Ser Ala
                        50                  55                  60

Pro Ala Ala Ser Leu Gly Ile Ser Thr Gly Asp Val Ile Thr Ala Val
             65                 70                  75                  80

Asp Gly Ala Pro Ile Asn Ser Ala Thr Ala Met Ala Asp Ala Leu Asn
                        85                  90                  95

Gly His His Pro Gly Asp Val Ile Ser Val Thr Trp Gln Thr Lys Ser
                        100                 105                 110

Gly Gly Thr Arg Thr Gly Asn Val Thr Leu Ala Glu Gly Pro Pro Ala
                        115                 120                 125

<210> SEQ ID NO 19
<211> LENGTH: 34
<212> TYPE: DNA
<213> ORGANISM: Artificial Sequence
<220> FEATURE:
<223> OTHER INFORMATION: Description of Artificial Sequence:5'
      oligonucleotide primer, HindIII site, for PCR
      amplification of human mammaglobin

<400> SEQUENCE: 19
gcgaagctta tgaagttgct gatggtcctc atgc                                    34

<210> SEQ ID NO 20
<211> LENGTH: 36
<212> TYPE: DNA
<213> ORGANISM: Artificial Sequence
<220> FEATURE:
<223> OTHER INFORMATION: Description of Artificial Sequence:3'
      oligonucleotide primer, XhoI site, for PCR
      amplification of human mammaglobin

<400> SEQUENCE: 20
cggctcgagt taaataaat cacaaagact gctgtc                                   36

<210> SEQ ID NO 21
<211> LENGTH: 7
<212> TYPE: PRT
<213> ORGANISM: Artificial Sequence
<220> FEATURE:
<223> OTHER INFORMATION: Description of Artificial Sequence:Met-His tag
      6aa

<400> SEQUENCE: 21

Met His His His His His His
 1               5

<210> SEQ ID NO 22
<211> LENGTH: 4
<212> TYPE: PRT
<213> ORGANISM: Artificial Sequence
<220> FEATURE:
<223> OTHER INFORMATION: Description of Artificial Sequence:enterokinase
      recognition site

<400> SEQUENCE: 22

Asp Asp Asp Lys
 1
```

```
<210> SEQ ID NO 23
<211> LENGTH: 128
<212> TYPE: PRT
<213> ORGANISM: Mycobacterium tuberculosis
<220> FEATURE:
<223> OTHER INFORMATION: positions 1-128 of Ra12

<400> SEQUENCE: 23

Thr Ala Ala Ser Asp Asn Phe Gln Leu Ser Gln Gly Gly Gln Gly Phe
 1               5                  10                  15

Ala Ile Pro Ile Gly Gln Ala Met Ala Ile Ala Gly Gln Ile Arg Ser
            20                  25                  30

Gly Gly Gly Ser Pro Thr Val His Ile Gly Pro Thr Ala Phe Leu Gly
        35                  40                  45

Leu Gly Val Val Asp Asn Asn Gly Asn Gly Ala Arg Val Gln Arg Val
    50                  55                  60

Val Gly Ser Ala Pro Ala Ala Ser Leu Gly Ile Ser Thr Gly Asp Val
65                  70                  75                  80

Ile Thr Ala Val Asp Gly Ala Pro Ile Asn Ser Ala Thr Ala Met Ala
                85                  90                  95

Asp Ala Leu Asn Gly His His Pro Gly Asp Val Ile Ser Val Thr Trp
            100                 105                 110

Gln Thr Lys Ser Gly Gly Thr Arg Thr Gly Asn Val Thr Leu Ala Glu
        115                 120                 125
```

METHODS OF USING A *MYCOBACTERIUM TUBERCULOSIS* CODING SEQUENCE TO FACILITATE STABLE AND HIGH YIELD EXPRESSION OF THE HETEROLOGOUS PROTEINS

CROSS-REFERENCES TO RELATED APPLICATIONS

This application claims priority to provisional application U.S. Ser. No. 60/158,585, filed Oct. 7, 1999, the disclosure of which is herein incorporated by reference in its entirety.

TECHNICAL FIELD

The present invention relates generally to nucleic acid and amino acid sequences of a fusion polypeptide comprising a *Mycobacterium tuberculosis* polypeptide, and a heterologous polypeptide of interest, expression vectors and host cells comprising such nucleic acids, and methods for producing such fusion polypeptides. In particular, the invention relates to materials and methods of using such *M. tuberculosis* sequence as a fusion partner to facilitate the stable and high yield expression of recombinant heterologous polypeptides of both eukaryotic and prokaryotic origin.

BACKGROUND OF THE INVENTION

The advent of recombinant DNA technology has led to the molecular cloning of a large number of coding sequences or genes from diverse cell types. In order to study the function of these genes or to produce the products encoded by such sequences, these genes are inserted in expression vectors under the control of appropriate regulatory sequences. This transfer of the expression vector into a eukaryotic or prokaryotic host cell generally results in the expression of the encoded product which can be subsequently purified. Large-scale production of many gene products is particularly important in cases where such products are of medical or industrial value.

However, notwithstanding the advances in gene expression, certain coding sequences do not readily produce their products in stable form. For example, expression in *E. coli* of recombinant proteins could be problematic particularly for proteins with trans-membrane domains or extensive hydrophobic sequences. Moreover, recombinant proteins may not contain the N-terminal amino acid residues with the appropriate codon bias. Thus, there remains a need for improved materials and methods for the expression of recombinant proteins.

SUMMARY OF THE INVENTION

The present invention provides for the first time recombinant nucleic acid molecules that encode fusion polypeptides comprising a Ra12 polypeptide and a heterologous polypeptide, fusion polypeptides, expression vectors and host cells comprising the nucleic acid molecules. The present invention further provides methods of using such recombinant nucleic acid molecules, expression vectors, and host cells to produce stable and high yield expression of fusion polypeptides of interest.

In one aspect, the present invention provides recombinant nucleic acid molecules that encode a fusion polypeptide, the recombinant nucleic acid molecules comprising a Ra12 polynucleotide sequence and a heterologous polynucleotide sequence, wherein the Ra12 polynucleotide sequence hybridizes to SEQ ID NO:3 under stringent conditions. In one embodiment, the recombinant nucleic acid molecules comprise a Ra12 polynucleotide sequence which is located 5' to a heterologous polynucleotide sequence. In another embodiment, the recombinant nucleic acid molecules further comprise a polynucleotide sequence that encodes a linker peptide between the Ra12 polynucleotide sequence and the heterologous polynucleotide sequence, wherein the linker peptide may comprise a cleavage site. In yet another embodiment, the recombinant nucleic acid molecules encode fusion polypeptides which further comprise an affinity tag. In yet another embodiment, the recombinant nucleic acid molecules encode a fusion polypeptide comprising a DPPD, a WT1, a mammaglobin, or a H9-32A heterologous polypeptide. In yet another embodiment, the recombinant nucleic acid molecules comprise a Ra12 polynucleotide sequence comprising at least about 30 nucleotides, at least about 60 nucleotides, or at least about 100 nucleotides. In yet another embodiment, the recombinant nucleic acid molecules comprise a Ra12 polynucleotide sequence as shown in SEQ ID NO:3. In yet another embodiment, the recombinant nucleic acid molecules comprise a Ra12 polynucleotide sequence that encodes a Ra12 polypeptide as shown in SEQ ID NO:4, SEQ ID NO:17, SEQ ID NO:18 or SEQ ID NO:23.

In another aspect, the present invention provides expression vectors comprising a promoter operably linked to a recombinant nucleic acid molecule according to any one of embodiments described herein.

In yet another aspect, the present invention provides host cells comprising expression vectors according to any one of embodiments described herein. In a preferred embodiment, the host cell is *E. coli*.

In yet another aspect, the present invention provides fusion polypeptides comprising a Ra12 polypeptide and a heterologous polypeptide, wherein the Ra12 polypeptide is encoded by a Ra12 polynucleotide sequence that hybridizes to SEQ ID NO:3 under stringent hybridization conditions. In one embodiment, the Ra12 polypeptide comprises at least about 10 amino acids, at least about 30 amino acids, or at least about 100 amino acids. In another embodiment, the Ra12 polypeptide has a sequence as shown in SEQ ID NO:4, SEQ ID NO:17, SEQ ID NO:18 or SEQ ID NO:23.

In yet another aspect, the present invention provides methods of producing fusion polypeptides, the method comprising expressing in a host cell a recombinant nucleic acid molecule that encodes a fusion polypeptide, the fusion polypeptide comprising a Ra12 polypeptide and a heterologous polypeptide, wherein the Ra12 polypeptide is encoded by a Ra12 polynucleotide sequence that hybridizes to SEQ ID NO:3 under stringent conditions. In one embodiment, the method further comprises purifying fusion polypeptides after their expression. In another embodiment, the method further comprises cleaving a fusion polypeptide between a Ra12 polypeptide and a heterologous polypeptide.

These and other aspects of the present invention will become apparent upon reference to the following detailed description and attached drawings.

BRIEF DESCRIPTION OF THE DRAWINGS

FIGS. 1A and 1B illustrate a nucleotide sequence (SEQ ID NO:1) and an amino acid sequence (SEQ ID NO:2) of MTB32A.

FIG. 2 illustrates a nucleotide sequence (SEQ ID NO:3) and an amino acid sequence (SEQ ID NO:4) of Ra12.

FIG. 3 illustrates a recombinant nucleic acid sequence comprising a nucleotide sequence (SEQ ID NO:5) and an amino acid sequence (SEQ ID NO:6) of Ra12-DPPD fusion polypeptide.

FIGS. 4A, B and C illustrate a recombinant nucleic acid sequence comprising a nucleotide sequence (SEQ ID NO:7) and an amino acid sequence (SEQ ID NO:8) of Ra12-WT1 fusion polypeptide.

FIG. 5 illustrates a recombinant nucleic acid sequence comprising a nucleotide sequence (SEQ ID NO:9) and an amino acid sequence (SEQ ID NO:10) of Ra12-mammaglobin fusion polypeptide.

FIG. 6 illustrates a recombinant nucleic acid sequence comprising a nucleotide sequence (SEQ ID NO:11) and an amino acid sequence (SEQ ID NO:12) of Ra12 H9 32A fusion polypeptide.

FIG. 7 illustrates Ra12(short) polypeptide (SEQ ID NO:17), which has amino acids 1–30 of SEQ ID NO:4.

FIG. 8 illustrates Ra12(long) polypeptide (SEQ ID NO:18), which has 128 amino acids of SEQ ID NO:4.

FIG. 9 illustrates a construct of Ra12 (short) polynucleotide fused to a human mammaglobin gene (Met-His tag 6aa=SEQ ID NO:21).

DETAILED DESCRIPTION OF THE INVENTION

As noted above, the present invention provides for the first time recombinant nucleic acid molecules, expression vectors, host cells, fusion polypeptides, and methods for producing fusion polypeptides, using a *Mycobacterium tuberculosis* coding sequence, namely a Ra12 nucleic acid which is a subsequence of a MTB32A nucleic acid. In particular, the invention provides materials and methods for using Ra12 sequences as a fusion partner to facilitate the stable and high yield expression of recombinant heterologous polypeptides of both eukaryotic and prokaryotic origin.

MTB32A is a serine protease of 32 KD molecular weight encoded by a gene in virulent and avirulent strains of *M. tuberculosis*. The complete nucleotide sequence (SEQ ID NO:1) and amino acid sequence (SEQ ID NO:2) of MTB32A are disclosed in FIG. 1. See, also, Skeiky et al., *Infection and Immun.* (1999) 67:3998–4007, incorporated herein by reference. This protein is naturally secreted into the supernatant of bacterial cultures. The open reading frame of the coding sequence contains N-terminal hydrophobic secretory signals. It stimulates peripheral blood mononuclear cells from healthy purified protein derivative (PPD)-positive donors to proliferate and secrete interferon. Thus, MTB32A is a candidate antigen for use in vaccine development against tuberculosis.

Figure 4A:
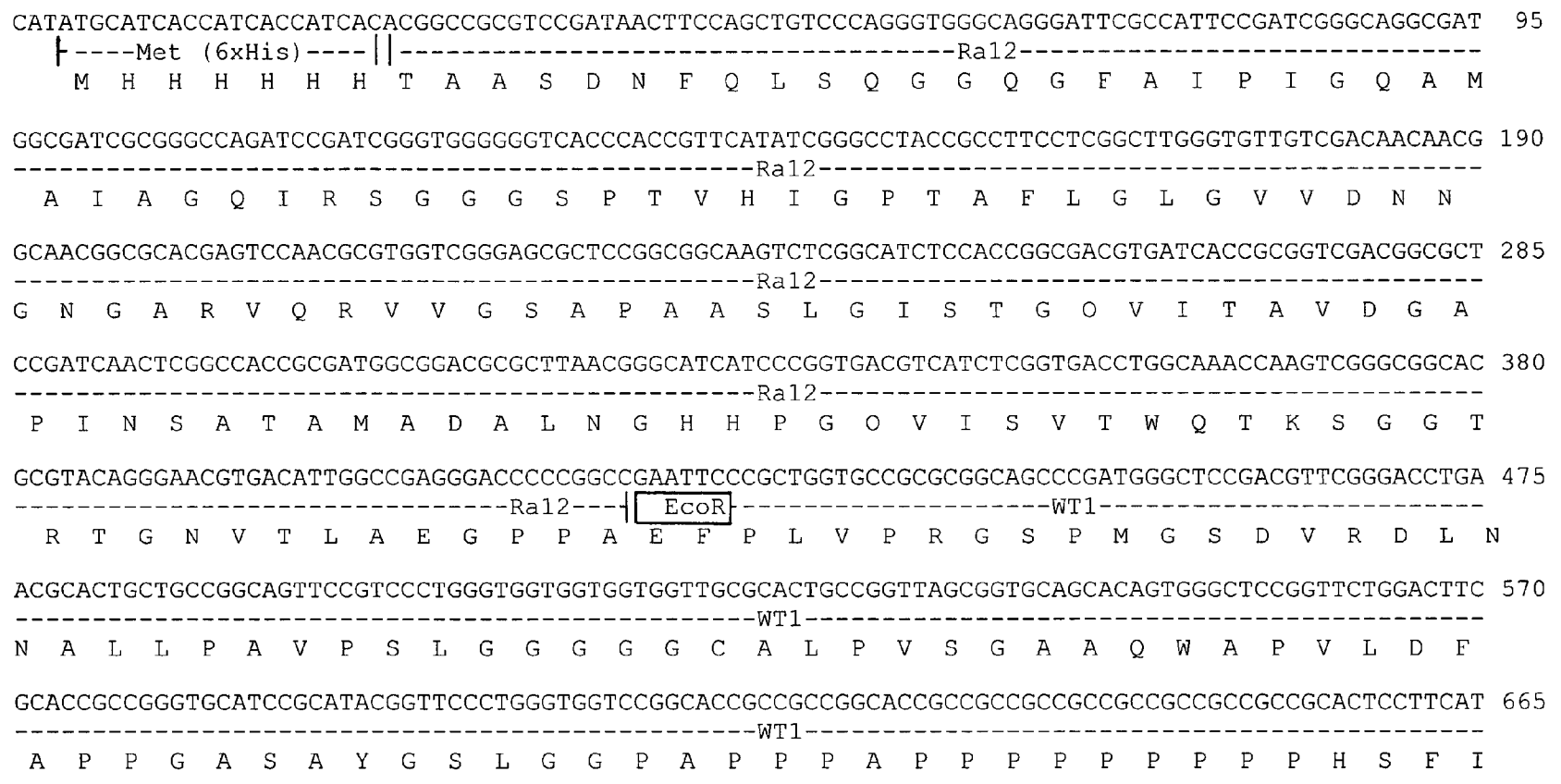

Surprisingly, it was discovered by the present inventors that a 14 KD C-terminal fragment of the MTB32A coding sequence expresses at high levels on its own and remains as a soluble protein throughout the purification process. This 14 KD C-terminal fragment of the MTB32A is referred herein as Ra12 (having amino acid residues 192 to 323 of MTB32A). The nucleic acid and amino acid sequences of native Ra12 are shown, e.g., in FIGS. 2–6. As described in detail below, the term "Ra12 polypeptide" or "Ra12 polynucleotide" as used herein refer to the native Ra12 sequences (e.g., SEQ ID NO:3 or SEQ ID NO:4), their variants, or fragments thereof (e.g., SEQ ID NO:17, SEQ ID NO:18 or SEQ ID NO:23). The present invention utilizes these properties of Ra12 polypeptides and provides recombinant nucleic acid molecules, expression vectors, host cells, and methods for stable and high yield expression of fusion polypeptides comprising a Ra12 polypeptide and a heterologous polypeptide of interest. The materials and methods of the present invention are particularly useful in expressing certain heterologous polypeptides (e.g., DPPD) that other conventional expression methods failed to express in any substantial quantity.

Recombinant Fusion Nucleic Acids

Recombinant nucleic acids, which encode a fusion polypeptide comprising a Ra12 polypeptide and a heterologous polypeptide of interest, can be readily constructed by conventional genetic engineering techniques. Recombinant nucleic acids are constructed so that, preferably, a Ra12 polynucleotide sequence is located 5' to a selected heterologous polynucleotide sequence. It may also be appropriate to place a Ra12 polynucleotide sequence 3' to a selected heterologous polynucleotide sequence or to insert a heterologous polynucleotide sequence into a site within a Ra12 polynucleotide sequence.

In the present invention, any suitable heterologous polynucleotide of interest can be selected as a fusion partner to Ra12 nucleic acids to produce a fusion polypeptide. A "heterologous sequence" or a "heterologous nucleic acid," as used herein, is one that originates from a source foreign to the particular host cell, or, if from the same source, is modified from its original form. Thus, a heterologous nucleic acid in a prokaryotic host cell includes a heterologous nucleic acid that is endogenous to particular host cell that has been modified. Modification of the heterologous sequence may occur, e.g., by treating the DNA with a restriction enzyme to generate a DNA fragment that is capable of being operably linked to the promoter. Techniques such as site-directed mutagenesis are also useful in modifying a heterologous sequence.

A heterologous nucleic acid from both eukaryotic and prokaryotic origins can be selected as a fusion partner. These nucleic acids include, but are not limited to, nucleic acids that encode pathogenic antigens, bacterial antigens, viral antigens, cancer antigens, tumor antigens, and tumor suppressors. Exemplary heterologous nucleic acids of interest include DPPD, WT1, mammaglobin, H9-32A nucleic acids, and other *Mycobacterium tuberculosis* nucleic acids (see, e.g., Cole et al. *Nature* (1999) 393:537–544; http://www.sanger.ac.uk; and http://www.pasteur.fr/mycdb/ for the complete genome sequences of *M. tuberculosis*; see, also WO98/53075 and WO98/53076, both of which are published on Nov. 26, 1998 for nucleic acid sequences that encode *M. tuberculosis* proteins). Any one of the nucleic acids disclosed herein can be used alone or in combination as a heterologous nucleic acid that can be selected as a fusion partner.

In addition, any suitable Ra12 polynucleotide (e.g., native Ra12 polynucleotide having SEQ ID NO:3, variants or fragments thereof) can be used in constructing recombinant fusion nucleic acids of the present invention. Preferred Ra12 polynucleotides comprise at least about 15 consecutive nucleotides, at least about 30 nucleotides, at least about 60 nucleotides, at least about 100 nucleotides, at least about 200 nucleotides, or at least about 300 nucleotides. Polynucleotides may be single-stranded or double-stranded, and may be DNA (genomic, cDNA or synthetic) or RNA molecules.

In one embodiment, the Ra12 polynucleotide sequence is as shown in SEQ ID NO:3. In another embodiment, the Ra12 polynucleotide sequence encodes a Ra12 polypeptide as shown in SEQ ID NO:4. In some embodiments, the Ra12 polynucleotide sequence comprises a portion of SEQ ID NO:3 or encodes a portion of SEQ ID NO:4. For instance, a Ra12 polynucleotide comprising 90 nucleotides (e.g., nucleotides 1–90 of SEQ ID NO:3), or a Ra12 polynucleotide comprising 384 nucleotides (e.g., nucleotides 1–384 of SEQ ID NO:3) can be used as a fusion partner. See Examples 2 and 3 below. Polynucleotides may comprise a native sequence (i.e., an endogenous sequence that encodes a Ra12 polypeptide SEQ ID NO:3 or a portion thereof) or may comprise a variant of such a sequence. Polynucleotide variants may contain one or more substitutions, additions, deletions and/or insertions such that the biological activity of the encoded fusion polypeptide is not diminished, relative to a fusion polypeptide comprising a native Ra12 polypeptide. Variants preferably exhibit at least about 70% identity, more preferably at least about 80% identity and most preferably at least about 90% identity to a polynucleotide sequence that encodes a native Ra12 polypeptide (SEQ ID NO:4) or a portion thereof. Optionally, the identity exists over a region that is at least about 25 to about 50 nucleotides in length, at least about 75–100 nucleotides in length, or a nucleotide sequence encoding at least about 25 to about 50 amino acids, or a nucleotide sequence encoding at least about 75–100 amino acids.

Two polynucleotide or polypeptide sequences are said to be "identical" if the sequence of nucleotides or amino acids in the two sequences is the same when aligned for maximum correspondence as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Research Foundation, Washington D.C. Vol. 5, Suppl. 3, pp. 345–358; Hein J. (1990) Unified Approach to Alignment and Phylogenes pp. 626–645 *Methods in Enzymology* vol. 183, Academic Press, Inc., San Diego, Calif.; Higgins, D. G. and Sharp, P. M. (1989) CABIOS 5:151–153; Myers, E. W. and Muller W. (1988) CABIOS4:11–17; Robinson, E. D. (1971) *Comb. Theor* 11:105; Santou, N. Nes, M. (1987) *Mol. Biol. Evol.* 4:406–425; Sneath, P. H. A. and Sokal, R. R. (1973) *Numerical Taxonomy—the Principles and Practice of Numerical Taxonomy*, Freeman Press, San Francisco, Calif.; Wilbur, W. J. and Lipman, D. J. (1983) *Proc. Natl. Acad., Sci. USA* 80:726–730.

Alternatively, optimal alignment of sequences for comparison may be conducted by the local identity algorithm of Smith and Waterman (1981) *Add. APL. Math* 2:482, by the identity alignment algorithm of Needleman and Wunsch (1970) *J. Mol. Biol.* 48:443, by the search for similarity methods of Pearson and Lipman (1988) *Proc. Natl. Acad. Sci. USA* 85: 2444, by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

Preferred examples of algorithms that are suitable for determining percent sequence identity and sequence similarity are the BLAST and BLAST 2.0 algorithms, which are described in Altschul et al. (1977) *Nucl. Acids Res.* 25:3389–3402 and Altschul et al. (1990) *J. Mol. Biol.* 215:403–410, respectively. BLAST and BLAST 2.0 can be used, for example with the parameters described herein, to determine percent sequence identity for the polynucleotides and polypeptides of the invention. Software for performing BLAST analyses is publicly available through the National Center for Biotechnology Information. For amino acid sequences, a scoring matrix can be used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment.

In one preferred approach, the "percentage of sequence identity" is determined by comparing two optimally aligned sequences over a window of comparison of at least 20 positions, wherein the portion of the polypeptide sequence in the comparison window may comprise additions or deletions (i.e., gaps) of 20 percent or less, usually 5 to 15 percent, or 10 to 12 percent, as compared to the reference sequences (which do not comprise additions or deletions) for optimal alignment of the two sequences. The percentage is calculated by determining the number of positions at which the identical amino acid residue occurs in both sequences to yield the number of matched positions, dividing the number of matched positions by the total number of positions in the reference sequence (i.e., the window size) and multiplying the results by 100 to yield the percentage of sequence identity.

Variants may also, or alternatively, be substantially homologous to a native Ra12 polynucleotide (e.g., SEQ ID NO:3), or a portion or complement thereof. Such polynucleotide variants are capable of hybridizing under stringent conditions to a naturally occurring DNA sequence encoding a native Ra12 polynucleotide (or a complementary sequence).

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5–10° C. lower than the thermal melting point ($T_m$) for the specific sequence at a defined ionic strength and pH. The $T_m$ is the temperature (under defined ionic strength, pH, and nucleic acid concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with a wash in 0.2×SSC, and 0.1% SDS at 65° C.

It will be appreciated by those of ordinary skill in the art that, as a result of the degeneracy of the genetic code, there are many nucleotide sequences that encode a Ra12 polypeptide as described herein. Some of these polynucleotides bear minimal homology to the nucleotide sequence of any native gene. Nonetheless, polynucleotides that vary due to differences in codon usage are specifically contemplated by the present invention. Further, alleles of the genes comprising the polynucleotide sequences provided herein are within the scope of the present invention. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

Thus, the terms such as "Ra12 polynucleotide" or "Ra12 polynucleotide sequence" as used herein refer to native Ra12 polynucleotide sequences (e.g., SEQ ID NO:3), fragments thereof, or any variants thereof. Functionally, any Ra12 polynucleotide has the ability to produce a fusion protein, and its ability to produce a fusion proteins in host cells may be enhanced or unchanged, relative to the native Ra12 polynucleotide (e.g., SEQ ID NO:3), or may be diminished by less than 50%, and preferably less than 20%, relative to the native Ra12 polynucleotide.

Nucleic acids encoding Ra12 polypeptides of this invention can be prepared by any suitable method known in the art. Exemplary methods include cloning and restriction of appropriate sequences or direct chemical synthesis by methods such as the phosphotriester method of Narang et al. (1979) *Meth. Enzymol.* 68: 90–99; the phosphodiester method of Brown et al. (1979) *Meth. Enzymol.* 68: 109–151; the diethylphosphoramidite method of Beaucage et al. (1981) *Tetra. Lett.*, 22: 1859–1862; and the solid support method of U.S. Pat. No. 4,458,066.

In one embodiment, a nucleic acid encoding MTB32A or Ra12 is isolated by routine cloning methods. Nucleotide sequences of MTB32A or Ra12 as provided herein are used to provide probes that specifically hybridize to other MTB32A or Ra12 nucleic acids in a genomic DNA sample, or to a MTB32A mRNA or Ra12 mRNA in a total RNA sample (e.g., in a Southern or Northern blot). Once the target MTB32A or Ra12 nucleic acids are identified, it can be isolated according to standard methods known to those of skill in the art.

The desired nucleic acids can also be cloned using well known amplification techniques. Examples of protocols sufficient to direct persons of skill through in vitro amplification methods, including the polymerase chain reaction (PCR) the ligase chain reaction (LCR), Qβ-replicase amplification and other RNA polymerase mediated techniques are found in Berger, Sambrook, and Ausubel, as well as Mullis et al. (1987) U.S. Pat. No. 4,683,202; *PCR Protocols A Guide to Methods and Applications* (Innis et al. eds) Academic Press Inc. San Diego, Calif. (1990) (Innis); Arnheim & Levinson (Oct. 1, 1990) C&EN 36–47; *The Journal Of NIH Research* (1991) 3: 81–94; (Kwoh et al. (1989) *Proc. Natl. Acad. Sci. USA* 86: 1173; Guatelli et al. (1990) *Proc. Natl. Acad. Sci. USA* 87: 1874; Lomell et al. (1989) *J. Clin. Chem.* 35: 1826; Landegren et al. (1988) *Science* 241: 1077–1080; Van Brunt (1990) *Biotechnology* 8: 291–294; Wu and Wallace (1989) *Gene* 4: 560; and Barringer et al. (1990) *Gene* 89: 117. Improved methods of cloning in vitro amplified nucleic acids are described in Wallace et al., U.S. Pat. No. 5,426,039. Suitable primers for use in the amplification of the nucleic acids of the invention can be designed based on the sequences provided herein.

The MTB32A or Ra12 nucleic acids can also be cloned by detecting their expressed product by means of assays based on the physical, chemical, or immunological properties of the expressed protein. For example, one can identify a cloned MTB32A or Ra12 nucleic acid by the ability of a polypeptide encoded by the nucleic acid to bind with antisera or purified antibodies made against the MTB32A or Ra12 polypeptides provided herein, which also recognize and selectively bind to the MTB32A or Ra12 homologs.

In some embodiments, it may be desirable to modify the MTB32A or Ra12 nucleic acids of the invention. Altered nucleotide sequences which can be used in accordance with the invention include deletions, additions or substitutions of different nucleotide residues resulting in a sequence that encodes the same or a functionally equivalent gene product. The gene product itself may contain deletions, additions or substitutions of amino acid residues, which result in a silent change thus producing a functionally equivalent antigenic epitope. Such conservative amino acid substitutions may be made on the basis of similarity in polarity, charge, solubility, hydrophobicity, hydrophilicity, and/or the amphipathic nature of the residues involved. Preferably, Ra12 nucleic acids that are shorter in length than SEQ ID NO:3 that encode biologically active fusion partner can be used. Such smaller functional equivalents of Ra12 polypeptides may be desirable to increase the amount of host cell resources that are available for the production of heterologous polypeptides of interest.

One of skill will recognize many ways of generating alterations in a given nucleic acid construct. Such well-known methods include site-directed mutagenesis, PCR amplification using degenerate oligonucleotides, exposure of cells containing the nucleic acid to mutagenic agents or radiation, chemical synthesis of a desired oligonucleotide (e.g., in conjunction with ligation and/or cloning to generate large nucleic acids) and other well-known techniques. See, e.g., Giliman and Smith (1979) *Gene* 8:81–97, Roberts et al. (1987) *Nature* 328: 731–734.

Recombinant nucleic acids that encode a fusion polypeptide comprising a Ra12 polypeptide and a selected heterologous polypeptide can be prepared using any methods known in the art. As described above, recombinant nucleic acids are constructed so that a Ra12 polynucleotide sequence is located in any suitable place in a construct. Preferably, a Ra12 polynucleotide sequence is located 5' to a selected heterologous polynucleotide sequence. Ra12 and heterologous polynucleotide sequences can also be modified to facilitate their fusion and subsequent expression of fusion polypeptides. For example, the 3' stop codon of the Ra12 polynucleotide sequence can be substituted with an in frame linker sequence, which may provide restriction sites and/or cleavage sites. The recombinant nucleic acids can further comprise other nucleotide sequences such as sequences that encode affinity tags to facilitate protein purification protocol.

Expression Vectors and Host Cells

The recombinant nucleic acids as described herein can be joined to a variety of other nucleotide sequences using established recombinant DNA techniques. For example, a polynucleotide can be cloned into any of a variety of cloning vectors, including plasmids, phagemids, lambda phage derivatives and cosmids. Vectors of particular interest include expression vectors, replication vectors, probe generation vectors and sequencing vectors. In general, a vector will contain an origin of replication functional in at least one organism, convenient restriction endonuclease sites and one or more selectable markers. Other elements will depend on the desired use, and will be apparent to those of ordinary skill in the art.

DNA sequences encoding the polypeptide components may be assembled separately, and ligated into an appropriate expression vector. The 3' end of the DNA sequence encoding one polypeptide component is ligated, with or without a polynucleotide sequence encoding a peptide linker, to the 5' end of a DNA sequence encoding the second polypeptide component so that the reading frames of the sequences are in phase. This permits translation into a single fusion protein that retains the biological activity of both component polypeptides.

The ligated DNA sequences are operably linked to suitable transcriptional or translational regulatory elements. The regulatory elements responsible for expression of DNA are located only 5' to the DNA sequence encoding the first polypeptides. Similarly, stop codons required to end translation and transcription termination signals are only present 3' to the DNA sequence encoding the second polypeptide.

Depending on the host/vector system utilized, any of a number of suitable transcription and translation elements, including constitutive and inducible promoters, may be used in the expression vector. For example, when cloning in bacterial systems, inducible promoters such as pL of bacteriophage λ, plac, ptrp, ptac (ptrp-lac hybrid promoter; cytomegalovirus promoter) and the like may be used; when cloning in yeast cell systems, promoters such as ADHI, PGK, PHO5, or the α factor promoter may be used; when cloning in insect cell systems, promoters such as the baculovirus polyhedron promoter may be used; when cloning in plant cell systems, promoters derived from the genome of plant cells (e.g., heat shock promoters; the promoter for the small subunit of RUBISCO; the promoter for the chlorophyll α/β binding protein) or from plant viruses (e.g., the 35S RNA promoter of cauliflower mosaic virus ("CaMV"); the coat protein promoter of tobacco mosaic virus ("TMV")) may be used; when cloning in mammalian cell systems, promoters derived from the genome of mammalian cells (e.g., metallothionein promoter) or from mammalian viruses (e.g., the adenovirus late promoter; the vaccinia virus 7.5K promoter) may be used; when generating cell lines that contain multiple copies of a the antigen coding sequence, SV40-, BPV- and EBV-based vectors may be used with an appropriate selectable marker.

A variety of host-expression vector systems may be utilized to express a Ra12 fusion protein coding sequences. These include, but are not limited to, microorganisms such as bacteria (e.g., E. coli, B. subtilis) transformed with recombinant bacteriophage DNA, plasmid DNA or cosmid DNA expression vectors containing a coding sequence; yeast (e.g., Saccharomycdes, Pichia) transformed with recombinant yeast expression vectors containing a coding sequence; insect cell systems infected with recombinant virus expression vectors (e.g., baculovirus) containing a coding sequence; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing a coding sequence; or cell systems (e.g., COS, CHO, BHK, 293, 3T3 cells transformed with suitable expression vectors). The expression elements of these systems vary in their strength and specificities.

Bacterial systems are preferred for the expression of Ra12 fusion polypeptides. Commonly used prokaryotic control sequences, which are defined herein to include promoters for transcription initiation, optionally with an operator, along with ribosome binding site sequences, include such commonly used promoters as the beta-lactamase (penicillinase) and lactose (lac) promoter systems (Change et al, *Nature* (1977) 198: 1056), the tryptophan (trp) promoter system (Goeddel et al., *Nucleic Acids Res.* (1980) δ: 4057), the tac promoter (DeBoer et al., *Proc. Natl. Acad. Sci. U.S.A.* (1983) 80:21–25); and the lambda-derived $P_L$ promoter and N-gene ribosome binding site (Shimatake et al., *Nature* (1981) 292: 128). The particular promoter system is not critical to the invention, any available promoter that functions in prokaryotes can be used.

Either constitutive or regulated promoters can be used in the present invention. Regulated promoters can be advantageous because the host cells can be grown to high densities before expression of the Ra12 fusion polypeptides is induced. High level expression of heterologous proteins slows cell growth in some situations. Regulated promoters especially suitable for use in *E. coli* include the bacteriophage lambda $P_L$ promoter, the hybrid trp-lac promoter (Amann et al., Gene (1983) 25: 167; de Boer et al., *Proc. Natl. Acad. Sci. USA* (1983) 80: 21, and the bacteriophage T7 promoter (Studier et al., *J. Mol. Biol.* (1986); Tabor et al., (1985). These promoters and their use are discussed in Sambrook et al., (1989) *Molecular Cloning: A Laboratory Manual,* 2nd Ed., Vols. 1–3, Cold Spring Harbor Laboratory.

For expression of Ra12 fusion polypeptides in prokaryotic cells other than *E. coli,* a promoter that functions in the particular prokaryotic species is required. Such promoters can be obtained from genes that have been cloned from the species, or heterologous promoters can be used. For example, the hybrid trp-lac promoter functions in *Bacillus* in addition to *E. coli.*

A ribosome binding site (RBS) is conveniently included in the expression cassettes of the invention. An RBS in *E. coli,* for example, consists of a nucleotide sequence 3–9 nucleotides in length located 3–11 nucleotides upstream of the initiation codon (Shine and Dalgarno, *Nature* (1975) 254: 34; Steitz, *In Biological regulation and development: Gene expression* (ed. R. F. Goldberger), vol. 1, p. 349, 1979, Plenum Publishing, NY).

When large quantities of the Ra12 fusion protein are to be produced, vectors which direct the expression of high levels of fusion protein products that are readily purified may be desirable. Such vectors include, but are not limited to, the *E. coli* expression vector pUR278 (Ruther et al. (1983) EMBO J. 2:1791), in which a coding sequence may be ligated into the vector in frame with the lacZ coding region so that a hybrid protein is produced; pIN vectors (Inouye and Inouye (1985) *Nucleic Acids Res.* 13:3101–3109; Van Heeke and Schuster (1989) *J. Biol. Chem.* 264:5503–5509); and the like. pGEX vectors may also be used to express foreign polypeptides as fusion proteins with glutathione S-transferase (GST). In general, such fusion proteins are soluble and can be purified easily from lysed cells by adsorption to glutathione-agarose beads followed by elution in the presence of free glutathione. For certain applications, it may be desirable to cleave the heterologous polypeptide of interest from the Ra12 fusion polypeptide after purification. This can be accomplished by any of several methods known in the art. For example, the pGEX vectors are designed to include thrombin or factor Xa protease cleavage sites so that the cloned fusion polypeptide of interest can be released from the GST moiety. See, e.g., Sambrook et al., supra.; Itakura et al., Science (1977) 198:1056; Goeddel et al., Proc. Natl. Acad. Sci. USA (1979) 76:106; Nagai et al., Nature (1984) 309:810; Sung et al., Proc. Natl. Acad. Sci. USA (1986) 83:561. Cleavage sites can be engineered into the recombinant nucleic acids for the fusion proteins at the desired point of cleavage.

Fusion Polypeptides

Within the context of the present invention, a "fusion" polypeptide comprises at least two parts: a Ra12 polypeptide as described herein, and a heterologous polypeptide of interest. In a fusion polypeptide, a Ra12 polypeptide is preferably fused, directly or indirectly, to the amino terminus of a heterologous polypeptide of interest, although fusion to the carboxy terminus of the heterologous polypeptide or insertion of the heterologous polypeptide into a site within an Ra12 polypeptide may also be appropriate.

Any heterologous polypeptide of interest, either eukaryotic or prokaryotic origins, can be selected as a fusion partner to a Ra12 polypeptide. These heterologous polypeptides include, but are not limited to, pathogenic antigens, bacterial antigens, viral antigens, cancer antigens, tumor antigens, and tumor suppressors. Exemplary heterologous polypeptides include DPPD, WT1, mammaglobin, H9-32A polypeptides, or other M. tuberculosis proteins. Any one of these polypeptides can be used alone or in combination as a heterologous polypeptide that can be selected as a fusion partner.

As noted above, a fusion polypeptide may comprise a native Ra12 polypeptide (e.g., SEQ ID NO:4), a variant thereof, or a fragment thereof. A polypeptide "variant," as used herein, is a polypeptide that differs from a native Ra12 polypeptide in one or more substitutions, deletions, additions and/or insertions, such that the biological activity of the polypeptide is not substantially diminished. In other words, the ability of a variant to produce fusion polypeptide in host cells may be enhanced or unchanged, relative to the native Ra12 protein, or may be diminished by less than 50%, and preferably less than 20%, relative to the native Ra12 protein. Such variants may generally be identified by modifying one of the above polypeptide sequences and evaluating the level of fusion polypeptide production in host cells, such as in E. coli. Exemplary variants include those in which a small portion (e.g., 1–30 amino acids, preferably 5–15 amino acids) has been removed from the N- and/or C-terminal of the native Ra12 polypeptides. In one embodiment, variants of native Ra12 polypeptides comprise at least about 5 amino acids, at least about 10 amino acids, at least about 30 amino acids, at least about 50 amino acids, or at least about 100 amino acids.

In one embodiment, the Ra12 polypeptide sequence is as shown in SEQ ID NO:4. In another embodiments, the Ra12 polypeptide sequence comprises a portion of SEQ ID NO:4. For instance, an Ra12 polypeptide comprising 30 amino acids (e.g., amino acids 1–30 of SEQ ID NO:4; SEQ ID NO:17) or an Ra12 polypeptide comprising 128 amino acids (e.g., 128 amino acids of SEQ ID NO:4; SEQ ID NO:18 or SEQ ID NO:23) can be used as a fusion partner. See Examples 2 and 3 below.

Polypeptide variants preferably exhibit at least about 70%, more preferably at least about 80% or at least about 90%, and most preferably at least about 95% identity (determined as described above) to the identified polypeptides. Optionally, identity exists over a region that is at least about 20 to about 50 amino acids in length, or optionally over a region that is 75–100 amino acids in length.

Preferably, a variant contains conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. Amino acid substitutions may generally be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. A variant may also, or alternatively, contain nonconservative changes. In a preferred embodiment, variant polypeptides differ from a native sequence by substitution, deletion or addition of five amino acids or fewer. Variants may also (or alternatively) be modified by, for example, the deletion or addition of amino acids that have minimal influence on the immunogenicity, secondary structure and hydropathic nature of the polypeptide.

Thus, the terms such as "Ra12 polypeptide" or "Ra12 polypeptide sequence" as used herein refer to native Ra12 polynucleotide sequences (e.g., SEQ ID NO:4), fragments thereof (e.g., SEQ ID NO:17, SEQ ID NO:18 or SEQ ID NO:23), or any variants thereof. Functionally, a Ra12 polypeptide has the ability to produce a fusion protein, and its ability to produce a fusion proteins in host cells may be enhanced or unchanged, relative to the native Ra12 polypeptide (e.g., SEQ ID NO:4), or may be diminished by less than 50%, and preferably less than 20%, relative to the native Ra12 polypeptide.

As noted above, fusion polypeptides may be conjugated to a linker or other sequence for ease of synthesis, purification or identification of the polypeptide or to enhance binding of the polypeptide to a solid support. For example, a peptide linker sequence may be employed to separate a Ra12 polypeptide and a heterologous polypeptide of interest by a distance sufficient to ensure that each polypeptide folds into its secondary and tertiary structures. Such a peptide linker sequence is incorporated into the fusion protein using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. In certain embodiments, peptide linker sequences may contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39–46, 1985; Murphy et al., *Proc. Natl. Acad. Sci. USA* 83:8258–8262, 1986; U.S. Pat. No. 4,935,233 and U.S. Pat. No. 4,751,180. The linker sequence may generally be from 1 to about 50 amino acids in length. Linker sequences are not required when the first and second polypeptides have non-essential N-terminal amino acid regions that can be used to separate the functional domains and prevent steric interference.

In a preferred embodiment, a linker can provide a specific cleavage site between a Ra12 polypeptide and a heterologous polypeptide of interest. Such a cleavage site may contain a target for proteolytic enzyme that includes, for example, enterokinase, Factor Xa, trypsin, collagenase, thrombin, ubiquitin hydrolase; or for chemical cleavage agents such as, for example, cyanogen bromide or hydroxyamine.

A fusion polypeptide may optionally contain an affinity tag which is linked to the fusion polypeptide so that the purification of recombinant polypeptides can be simplified. For example, multiple histidine residues encoded by the tag allow the use of metal chelate affinity chromatography methods for the purification of fusion polypeptides. Other examples of affinity tag molecules include, Strep-tag, Pin-Point, maltose binding protein, glutathione S-transferase, etc. See, e.g., Glick and Pasternak (1999) *Molecular Biotechnology Principles and Applications of Recombinant DNA,* $2^{nd}$ Ed., American Society for Microbiology, Washington, D.C.

Fusion polypeptides may be prepared using any of a variety of well known techniques. Recombinant fusion polypeptides encoded by DNA sequences as described above may be readily prepared from the DNA sequences using any of a variety of expression vectors known to those of ordinary skill in the art. Expression may be achieved in any appropriate host cell that has been transformed or transfected with an expression vector containing a DNA molecule that encodes a recombinant polypeptide. Suitable host cells include prokaryotes, yeast and higher eukaryotic cells described above. Preferably, the host cell employed is *E. coli*. Supernatants from suitable host/vector systems which secrete recombinant protein or polypeptide into culture media may be first concentrated using a commercially available filter. Following concentration, the concentrate may be applied to a suitable purification matrix such as an affinity matrix or an ion exchange resin. Finally, one or more reverse phase HPLC steps can be employed to further purify a recombinant polypeptide.

Portions and other variants having fewer than about 100 amino acids, and generally fewer than about 50 amino acids, may also be generated by synthetic means, using techniques well known to those of ordinary skill in the art. For example, such polypeptides may be synthesized using any of the commercially available solid-phase techniques, such as the Merrifield solid-phase synthesis method, where amino acids are sequentially added to a growing amino acid chain. See Merrifield, *J. Am. Chem. Soc.* 85:2149–2146, 1963. Equipment for automated synthesis of polypeptides is commercially available from suppliers such as Perkin Elmer/Applied BioSystems Division (Foster City, Calif.), and may be operated according to the manufacturer's instructions.

In general, polypeptides (including fusion proteins) and polynucleotides as described herein are isolated. An "isolated" polypeptide or polynucleotide is one that is removed from its original environment. For example, a naturally-occurring protein is isolated if it is separated from some or all of the coexisting materials in the natural system. Preferably, such polypeptides are at least about 90% pure, more preferably at least about 95% pure and most preferably at least about 99% pure. A polynucleotide is considered to be isolated if, for example, it is cloned into a vector that is not a part of the natural environment.

In addition to providing stable and high yield expression of fusion polypeptides of interest, the recombinant fusion nucleic acids and fusion polypeptides of the invention can be used in a number of other methods. For example, the fusion polypeptide coding sequence of the invention can be used to encode a protein product for use as an antigen for detecting serum antibodies. For example, the presence of serum antibodies to *M. tuberculosis* antigens in an individual indicates that the individual is infected with *M. tuberculosis*. In standard diagnostic tests, serum antibodies to *M. tuberculosis* are detected by monitoring binding of serum antibodies to *M. tuberculosis* proteins. The fusion polypeptides of the invention are useful as sources of proteins for monitoring binding of serum antibodies to fusion proteins.

Alternatively, the fusion polypeptide can be used as an immunogen to induce and/or enhance immune responses. Such coding sequences can be ligated with a coding sequence of another molecule such as a *M. tuberculosis* antigen, a cytokine or an adjuvant. Such polynucleotides may be used in vivo as a DNA vaccine (U.S. Pat. Nos. 5,589,466; 5,679,647; and 5,703,055). Alternatively, purified or partially purified fusion polypeptides or fragments may be used as vaccines or therapeutic compositions. Any of a variety of methods known in the art can be employed to produce vaccines or therapeutic compositions comprising the fusion polypeptides of the present invention.

Protein Purification and Preparations

Once a recombinant protein is expressed, it can be identified by assays based on the physical or functional properties of the product, including radioactive labeling of the product followed by analysis by gel electrophoresis, radioimmunoassay, ELISA, bioassays, etc.

Once the encoded protein is identified, it may be isolated and purified by standard methods including chromatography (e.g., high performance liquid chromatography, ion exchange, affinity, and sizing column chromatography), centrifugation, differential solubility, or by any other standard technique for the purification of proteins. See, generally, R. Scopes, *Protein Purification*, Springer-Verlag, N.Y. (1982), Deutscher, *Methods in Enzymology Vol. 182: Guide to Protein Purification*, Academic Press, Inc. N.Y. (1990). The actual conditions used will depend, in part, on factors such as net charge, hydrophobicity, hydrophilicity, etc., and will be apparent to those having skill in the art. The functional properties may be evaluated using any suitable assays.

The functional properties of the fusion protein may be evaluated using any suitable assay such as antibody binding, induction of T cell proliferation, stimulation of cytokine production such as IL2, IL-4 and IFN-γ. For the practice of the present invention, it is preferred that each fusion protein is at least 80% purified from other proteins. It is more preferred that they are at least 90% purified. For in vivo administration, it is preferred that the proteins are greater than 95% purified.

The purified proteins may be further processed before use. For example, the proteins may digested with a specific enzyme to separate the Ra12 polypeptide from the heterologous polypeptide.

One of skill would recognize that modifications can be made to the recombinant nucleic acids and fusion polypeptides without diminishing their biological activity. Some modifications may be made to facilitate the cloning, expression, or incorporation of the tag molecule into a fusion polypeptide. Such modifications are well known to those of skill in the art and include, for example, a methionine added at the amino terminus to provide an initiation site, or additional amino acids (e.g., polyHistidine ("poly His")) placed on either terminus to create conveniently located restriction sites or termination codons or purification sequences.

The following Examples are offered by way of illustration and not by way of limitation.

EXAMPLES

The following examples describe experiments that illustrate that Ra12 fusion constructs produced stable and high yield expression of fusion polypeptides. The following examples also illustrate that various Ra12 sequences can be used as a fusion partner.

Example 1

The Full Length Ra12 Sequence (SEQ ID NO:4) as a Fusion Partner

A. Construction of Expression Vectors

Coding sequences of *M. tuberculosis* antigens were modified by PCR in order to facilitate their fusion and subsequent expression of fusion protein. pET 17b vector (Novagen) was modified to include Ra12, a 14 kDa C-terminal fragment of the serine protease antigen MTB32A of *M. tuberculosis*. The 3' stop codon of the Ra12 sequence was substituted with an in frame EcoRI site and the N-terminal end was engineered to code for six His-tag residues immediately following the initiator Met to facilitate a simple one step purification protocol of Ra12 recombinant proteins by affinity chromatography over Ni-NTA matrix.

Specifically, the C-terminal fragment of antigen MTB32A was amplified by standard PCR methods using the oligonucleotide primers 5'CAA TTA CAT ATG CAT CAC CAT CAC CAT CAC ACG GCC GCG TCC GAT AAC TTC (SEQ ID NO:13) and the 3' oligonucleotide sequence is 5'-CTA ATC GAA TTC GGC CGG GGG TCC CTC GGC CAA (SEQ ID NO:14). The 450 bp product was digested with NdeI and EcoRI and cloned into the pET 17b expression vector similarly digested with the same enzymes. Expression of the recombinant Ra12 protein was accomplished following transformation into the *E. coli* BL-21 (pLysE) host cells (Novagen) and induction with IPTG. Following lysis of the *E. coli* cells and centrifugation at 10K rpm, recombinant Ra12 was found in the soluble supernatant fraction. Protein from the soluble supernatant was purified by affinity chromatography over an Ni-NTA column which remained soluble following dialysis in 1×PBS. The amount of purified protein obtained was routinely in the 60 to 100 mg per liter range.

DPPD sequence was engineered for expression as a fusion protein with Ra12 by designing oligonucleotide primers to specifically amplify the mature secreted form. The 5' oligonucleotide containing an enterokinase recognition site (DDDK; SEQ ID NO:22) has the sequences 5'-CAA TTA GAA TTC GAC GAC GAC GAC AAG GAT CCA CCT GAC CCG CAT CAG-3' (SEQ ID NO:15) and the 3' oligonucleotide sequence is 5'CAA TTA GAA TTC TCA GGG AGC GTT GGG CTG CTC (SEQ ID NO:16). The resulting PCR amplified product was digested with EcoRI and subcloned into the EcoRI site of the pET-Ra12 vector. Following transformation into the *E. Coli* host strain (XL1-blue; Stratagene), clones containing the correct size insert were submitted for sequencing in order to identify those that were in frame with the Ra12 fusion. Subsequently, the DNA of interest (FIG. 3) was transformed into the BL-21(pLysE) bacterial host and fusion protein expressed following induction of the culture with IPTG.

B. Expression and Purification of Fusion Proteins

The recombinant (His-tag) Ra12-DPPD fusion protein was purified from 500 ml of IPTG induced batch cultures from the soluble supernatant by affinity chromatography using the one step QIAexpress Ni-NTA Agarose matrix (QIAGEN, Chatsworth, Calif.) in the presence of 8M urea. Briefly, 20 ml of an overnight saturated culture of BL21 containing the pET construct was added into 500 ml of 2xYT media containing 50 ug/ml ampicillin and 34 ug/ml chloramphenicol, grown at 37° C. with shaking. The bacterial cultures were induced with 2 mM IPTG at an OD 560 of 0.3 and grown for an additional 3 h (OD 1.3 to 1.9). Cells were harvested from 500 ml batch cultures by centrifugation and resuspended in 20 ml of binding buffer (0.1 M sodium phosphate, pH 8.0; 10 mM Tris-HCl, pH 8.0) containing 2 mM PMSF and 20 ug/ml leupeptin. *E. coli* was lysed by adding 15 mg of lysozyme and rocking for 30 min at 4° C. following sonnication (4×30 sec). Lysed cells were spun at 12 k rpm for 30 min and urea was added directly to the supernatant at a final concentration of 8M.

The supernatant was batch bound to Ni-NTA agarose resin (5 ml resin per 500 ml inductions) by rocking at R/T for 1 h and the matrix passed over a column. The flow through was passed twice over the same column followed by three washes with 30 ml each of wash buffer (0.1 M sodium phosphate and 10 mM Tris-HCL, pH 6.3) also containing 8 M urea. Bound protein was eluted with 30 ml of 100 mM imidazole in wash buffer and 5 ml fractions collected. Fractions containing the recombinant antigen were pooled, dialyzed against 10 mM Tris-HCl (pH 8.0) bound one more time to the Ni-NTA matrix, eluted and dialyzed in 1×PBS (pH 7.4) or 10 mM Tris-HCL (pH 7.8). The yield of the purified recombinant fusion protein was in the 50 to 75 mg per liter of induced bacterial culture with greater than 95% purity representing a single band. Recombinant proteins were assayed for endotoxin contamination using the Limulus assay (BioWhittaker) and were shown to contain <10 E.U./mg (<1 ng LPS/mg).

C. Generation of Antiserum

The purified fusion protein (100 ug) was mixed with 100 ug of muramyl dipeptide, brought up to 1 ml with 1×PBS and emulsified with 1 ml IFA (incomplete freunds; Life Technologies) adjuvant. The emulsion was injected at multiple sites s.c. into a female New Zealand rabbit (R&R Rabbitry, Stanwood, Wash.). The rabbit was given two subsequent boosters (100 ug antigen in IFA) 6 weeks apart and a final i.v. shot with 100 ug of the recombinant protein again given after 6 weeks. One week after the final boost, the rabbit was sacrificed and serum was collected and stored at −20° C.

D. Immunoblotting Analysis

*M. tuberculosis* (strain H37Rv) total lysate or PPD (2.5 μg each) and 25 ng of the purified recombinant Ra12-DPPD fusion protein were separated by electrophoresis on 16% SDS-PAGE gels and transferred to nitrocellulose using a semi-dry transfer apparatus (BioRad). Blots, in duplicate, were blocked for a minimum of 1 hr with PBS/0.1% Tween and probed with polyclonal sera from the same rabbit prior to immunization or post immunization with the purified recombinant fusion protein (diluted 1:500 in PBS/0.1% Tween 20). Reactivity was assessed as previously using [$^{125}$I]—protein A, followed by autoradiography.

E. Results

Several expression systems were initially evaluated for the expression of DPPD in *E. coli*. This included sub-cloning of DPPD coding sequence as non-fusion constructs in 1) pET17b (Novagen) and pQ30 (Qiagen, Santa Clarita, Calif.) or 2) as fusion constructs using pET32A (Novagen, Madison, Wis.) or pGEX-2T (Pharmacia Biotech, Piscataway, N.J.). In all of these systems, very little if any DPPD was expressed and purified.

Figure 4C:
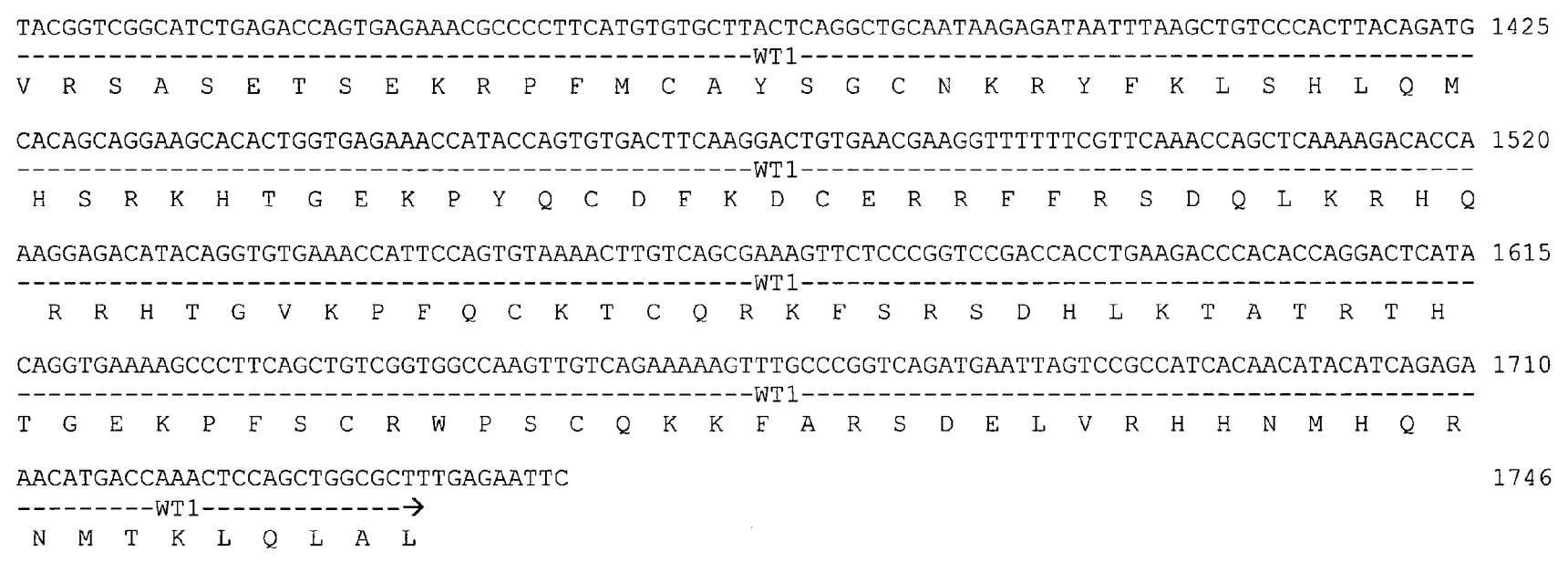
Figure 6B:
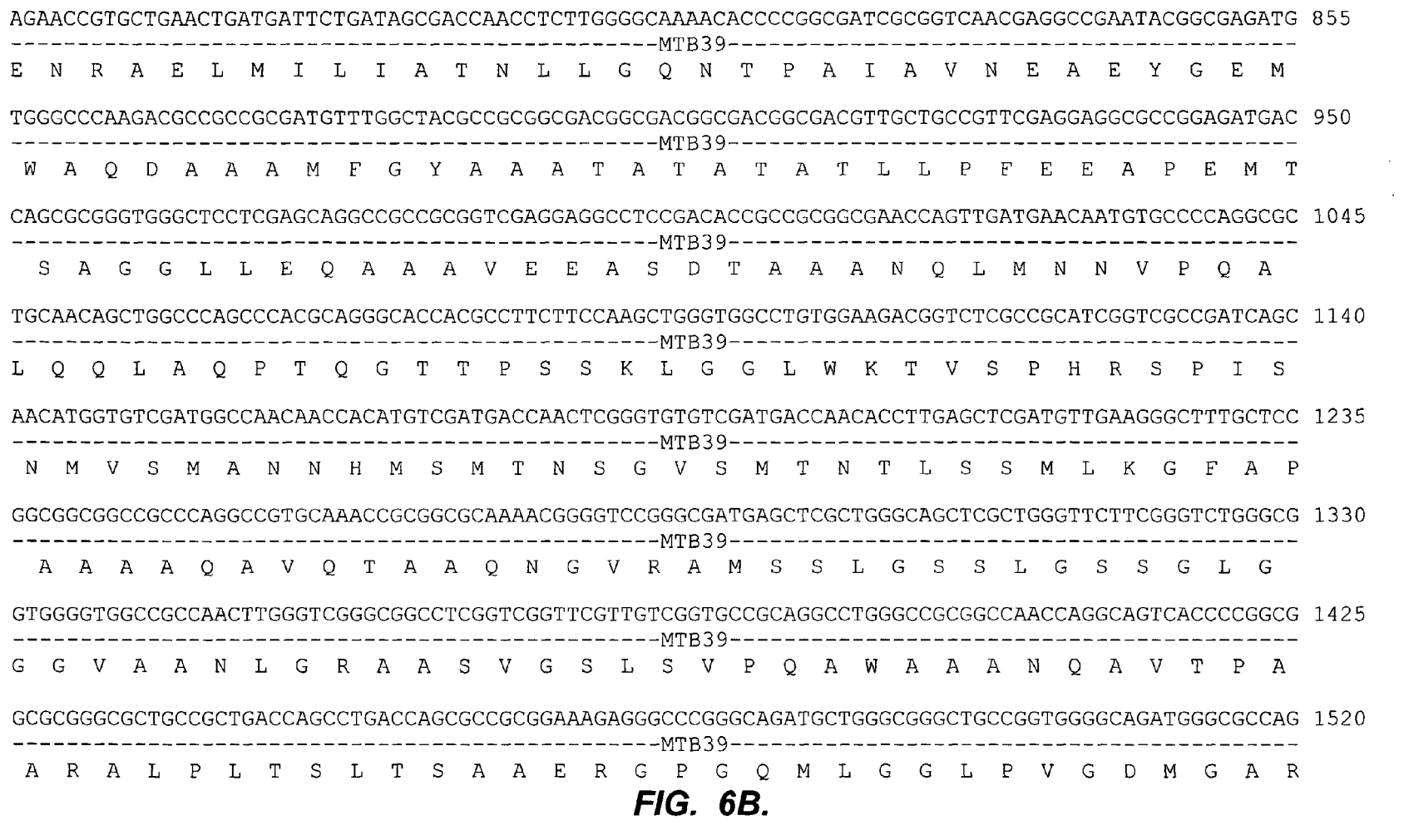
Figure 6C:
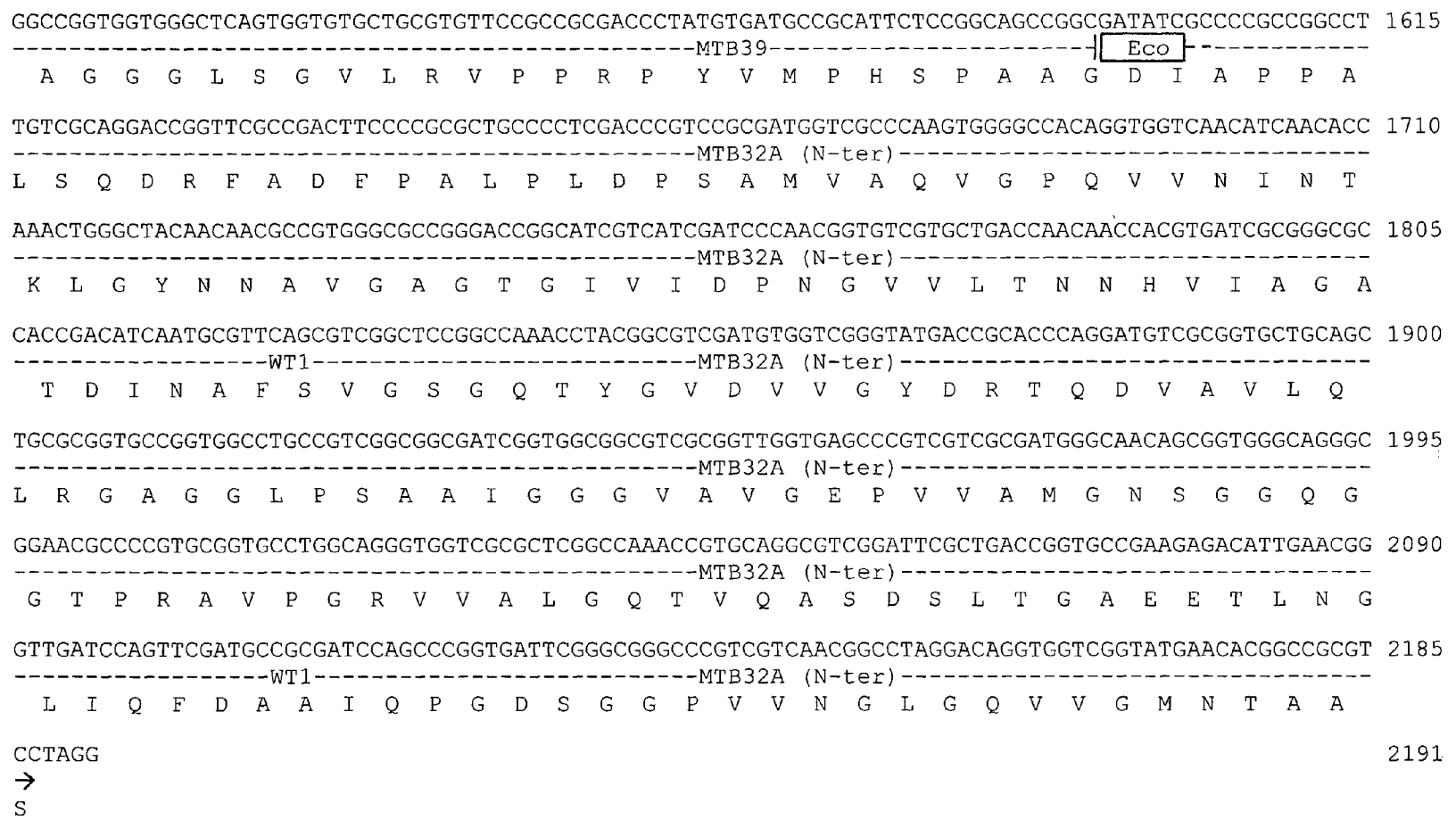

In contrast, when the DPPD coding sequence was inserted 3' to the Ra12 sequence in an expression vector and transformed into *E. coli*, a large amount of Ra12-DPPD fusion protein was produced. The nucleotide sequence (SEQ ID NO:5) and amino acid sequence (SEQ ID NO:6) of Ra12-DPPD are disclosed in FIG. 3. The immunogenicity of DPPD was maintained as evidenced by the ability of antiserum to react with the purified protein in immunoblotting analysis. In addition, three other proteins of eukaryotic or prokaryotic origin (see FIGS. 4–6) were also successfully expressed by the Ra12 fusion constructs. Thus, the Ra12 coding sequence is useful as a fusion partner in an expression construct to facilitate the expression of a heterologous sequence.

Example 2

Short Ra12 Polypeptide (SEQ ID NO:17) as a Fusion Partner

In this example, a Ra12 polypeptide comprising amino acids 1–30 of SEQ ID NO:4 was used as a fusion partner to link with the full length human mammaglobin gene. This short form of Ra12 polypeptide has the amino acid sequence shown in SEQ ID NO:17, and is referred to herein as "Ra12(short)".

As shown in FIG. 9, the 3' end of the Ra12(short) sequence is fused to the full length human mammaglobin gene. Specifically, the human mammaglobin gene was amplified by standard PCR methods using the following oligonucleotide primers: the 5' primer, Hind III site: 5'-gc-gaagcttATGAAGTTGCTGATGGTCCTCATGC-3' (SEQ ID NO:19); the 3' primer, XhoI site: 5'-cggctcgagT-TAAAATAAATCACAAAGACTGCTGTC-3' (SEQ ID NO:20). The 5' Hind III and 3' Xho I sites were added to assist subcloning into a vector. The N-terminal end of the fusion construct was engineered to code for six His-tag residues immediately following the Met to facilitate purification protocols. The expression of the fusion construct was accomplished following transformation into *E. coli* using procedures similar to those described in Example 1. Compared to a construct without a Ra12(short) sequence, the fusion construct with a Ra12(short) sequence substantially increased the expression of the fusion Ra12(short)-mammaglobin protein.

Example 3

Longer Ra12 Polypeptide (SEQ ID NO:18) as a Fusion Partner

In this example, a Ra12 polypeptide comprising 128 amino acids of SEQ ID NO:4 was used as a fusion partner to link with the full length human mammaglobin gene. This long form of Ra12 polypeptide has the amino acid sequence shown in SEQ ID NO:18, and is referred to herein as "Ra12(long)". Cloning and expression procedures similar those described in Example 2 were used. Compared to a construct without a Ra12(long) sequence. the fusion construct with a Ra12(long) sequence substantially increased the expression of the fusion Ra12(long)-mammaglobin protein.

The present invention is not to be limited in scope by the exemplified embodiments which are intended as illustrations of aspects of the invention, and any clones, nucleotide or amino acid sequences which are functionally equivalent are within the scope of the invention. Indeed, various modifications of the invention in addition to those described herein will become apparent to those skilled in the art from the foregoing description and accompanying drawings. Such modifications are intended to fall within the scope of the appended claims. It is also to be understood that all base pair sizes given for nucleotides are approximate and are used for purposes of description.

All publications cited herein are incorporated by reference in their entirety.

What is claimed is:

1. A recombinant nucleic acid molecule that encodes a fusion polypeptide, the recombinant nucleic acid molecule comprising a Ra12 polynucleotide sequence and a non-*Mycobacterium tuberculosis* polynucleotide sequence, wherein the Ra12 polynucleotide sequence encodes a Ra12 polypeptide consisting of the sequence set forth in SEQ ID NO:4, SEQ ID NO:17, SEQ ID NO:18, or SEQ ID NO:23.

2. The recombinant nucleic acid molecule according to claim 1, wherein the Ra12 polynucleotide sequence is located 5' to the non-*Mycobacterium tuberculosis* polynucleotide sequence.

3. The recombinant nucleic acid molecule according to claim 1, the recombinant nucleic acid molecule further comprising a polynucleotide sequence that encodes a linker peptide between the Ra12 polynucleotide sequence and the non-*Mycobacterium tuberculosis* polynucleotide sequence.

4. The recombinant nucleic acid molecule according to claim 3, wherein the linker peptide comprises a cleavage site.

5. The recombinant nucleic acid molecule according to claim 1, wherein the fusion polypeptide further comprises an affinity tag which is linked to the fusion polypeptide.

6. The recombinant nucleic acid molecule according to claim 1, wherein the non-*Mycobacterium tuberculosis* nucleic acid sequence encodes a WT1 or a mammaglobin polypeptide.

7. An expression vector comprising a promoter operably linked to a recombinant nucleic acid molecule according to claim 1.

8. A host cell transformed or transfected with an expression vector according to claim 7.

9. The host cell according to claim 8, wherein the host cell is *E. coli*.

10. The recombinant nucleic acid molecule according to claim 1, wherein the Ra12 polynucleotide sequence consists of the sequence set forth in SEQ ID NO:3.

11. The recombinant nucleic acid molecule according to claim 1, wherein the non-*Mycobacterium tuberculosis* polynucleotide sequence is a eukaryotic polynucleotide sequence.

12. A recombinant nucleic acid molecule that encodes a fusion polypeptide, the recombinant nucleic acid molecule comprising a Ra12 polynucleotide sequence and a non-*Mycobacterium tuberculosis* polynucleotide sequence, wherein the Ra12 polynucleotide sequence encodes a Ra12 polypeptide consisting of the sequence set forth in SEQ ID NO:17.

13. A recombinant nucleic acid molecule that encodes a fusion polypeptide, the recombinant nucleic acid molecule comprising a Ra12 polynucleotide sequence and a non-*Mycobacterium tuberculosis* polynucleotide sequence, wherein the Ra12 polynucleotide sequence encodes a Ra12 polypeptide consisting of the sequence set forth in SEQ ID NO:18.

14. A recombinant nucleic acid molecule that encodes a fusion polypeptide, the recombinant nucleic acid molecule comprising a Ra12 polynucleotide sequence and a non-*Mycobacterium tuberculosis* polynucleotide sequence, wherein the Ra12 polynucleotide sequence encodes a Ra12 polypeptide consisting of the sequence set forth in SEQ ID NO:4.

15. A method of producing a fusion polypeptide, the method comprising:
  expressing in a host cell a recombinant nucleic acid molecule that encodes a fusion polypeptide, the fusion polypeptide comprising a Ra12 polypeptide and a non-*Mycobacterium tuberculosis* polypeptide, wherein the Ra12 polypeptide consists of the sequence set forth in SEQ ID NO:4, SEQ ID NO:17, SEQ ID NO:18, or SEQ ID NO:23; and purifying the fusion polypeptide from the host cell.

16. The method according to claim 10, wherein the fusion polypeptide further comprises an affinity tag which is linked to the fusion polypeptide.

17. The method according to claim 10, wherein the host cell is *E. coli.*

18. The method according to claim 10, wherein the Ra12 polypeptide is encoded by a Ra12 polynucleotide sequence consisting of the sequence set forth in SEQ ID NO:3.

19. The method according to claim 10, wherein the non-*Mycobacterium tuberculosis* polypeptide is a eukaryotic polypeptide.

20. The method according to claim 15, wherein the Ra12 polypeptide consists of the sequence set forth in SEQ ID NO:4.

21. The method according to claim 15, wherein the Ra12 polypeptide sequence consists of the sequence set forth in SEQ ID NO:17.

22. The method according to claim 15, wherein the Ra12 polypeptide sequence consists of the sequence set forth in SEQ ID NO:18.

23. A recombinant nucleic acid molecule that encodes a fusion polypeptide, the recombinant nucleic acid molecule comprising a Ra12 polynucleotide sequence and a non-*Mycobacterium tuberculosis* polynucleotide sequence, wherein the Ra12 polynucleotide sequence encodes a Ra12 polypeptide consisting of the sequence set forth in SEQ ID NO:23.

24. The method according to claim 15, wherein the Ra12 polypeptide sequence consists of the sequence set forth in SEQ ID NO:23.

* * * * *